(12) United States Patent
Gill

(10) Patent No.: US 6,500,431 B1
(45) Date of Patent: Dec. 31, 2002

(54) INHIBITORS OF ANGIOGENESIS AND TUMOR GROWTH

(75) Inventor: Parkash S. Gill, Agoura, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/352,548

(22) Filed: Jul. 12, 1999

Related U.S. Application Data

(60) Provisional application No. 60/092,647, filed on Jul. 13, 1998.

(51) Int. Cl.[7] .......................... A61K 39/00; A61K 38/00
(52) U.S. Cl. ............................... 424/184.1; 424/185.1; 530/300
(58) Field of Search ...................... 530/300; 424/184.1, 424/277.1, 185.1

(56) References Cited

U.S. PATENT DOCUMENTS

| 5,696,080 A | | 12/1997 | O'Brien et al. |
| 5,910,568 A | * | 6/1999 | Hammerstedt et al. |

FOREIGN PATENT DOCUMENTS

| WO | 95/03821 | 2/1995 |
| WO | PCT/US97/00/05 | 7/1997 |

OTHER PUBLICATIONS

Liepinsh, Edvards et al., "Saposin Fold Revealed By the NMR Structure Of NK–lysin," (1997) *Nature Structural Biology*, vol. 4, No. 10, pp. 793–795.
Pointing, Christopher P. et al., "Swaposins: Circular Permutations Within Genes Encoding Saposin Homologues," (1995) *Trends In Biochemical Sciences*, vol. 20, No. 5, pp. 179–180.
Collard, Michael W. et al., "Biosynthesis and Molecular Cloning of Sulfated Glycoprotein 1 Secreted by Rat Sertoli Cells: Sequence Similarity with the 70–Kilodalton Precursor to Sulfatide/$G_{M1}$ Activator," (1988) *Biochemistry*, 27:4557–4564.
Hiraiwa, Masao et al., "The Effect of Carbohydrate Removal on Stability and Activity of Saposin B[1]," (1993) *Arch. Biochem. Biophys.* 303:326.
Kase, Ryoichi et al. "Only sphingolipid activator protein B(SAP–B or saposin B) stimulates the degradation of globotriaosylceramide by recombinant human Lysosomal α–galactosidase in a detergent–free liposomal system," (1996) *FEBS Lett.* 393:74–76.
Kretz, Keith A. et al., "Characterization of a mutation in a family with saposin B deficiency: A glycosylation site defect," (1990) *Proc. Nat'l Acad. Sci. USA*, 87:2541–2544.
Lamontagne, Sonia et al., "Modulation of Human Saposin B Sphingolipid–binding Specificity by Alternative Splicing," (1994) *Biol. Chem.*, 269:20528–20532.
Sano, Akira et al., "Sphingolipid Hydrolase Activator Proteins and Their Precursors," (1989) *Biochem. Biophys. Res. Commun.*, 165:1191–1197.
Zetter, Bruce R., "Angiogenesis And Tumor Metastasis," (1998) *Annu. Rev. Med.* 49:407–24.
Genbank Accession No.: AAA 60303 Prosaposin, 1995.
In re Johnson and Farnham, 194 USPQ 187, Bureau of National Affairs, Inc., Intellectual Property Law Library.*
Stevens et al. (Biochemistry, v32, 1993, pp. 4051–4059.*
Stevens et al. (A49475), Pir Sequence Database, National Center for Biotechnology Information, National Library of Medicine, Bethesda, Maryland, 1993.*
Gura, Science, v278, 1997, pp. 1041–1042.*
Bowie et al. Science, 247:1306–1310, 1990, p. 1306, col. 2.*
Reilly et al., Clin. Pharmacokinet., vol. 32, No. 4, 1997.*
Burgess et al., J of Cell Bio. 111:2129–2138, 1990.*
Lazar et al. Molecular and Cellular Biology 8:1247–1252, 1988.*

* cited by examiner

Primary Examiner—Anthony C. Caputa
Assistant Examiner—Gary B. Nickol
(74) *Attorney, Agent, or Firm*—Bingham McCutchen, LLP

(57) ABSTRACT

This invention provides for polypeptides that have surprising anti-angiogenic activity. These peptides are derived from Saposin B, a previously known protein involved in the hydrolysis of sphingolipids. In addition, methods of treating mammals with these anti-angiogenic polypeptides are provided, as well as the pharmaceutical compositions used to treat. Furthermore, the polypeptides of this invention can be used in fusion proteins, wherein the fusion proteins also comprise cell targeting or cytotoxic moieties. Also provided is the receptor to which these polypeptides bind.

39 Claims, 11 Drawing Sheets

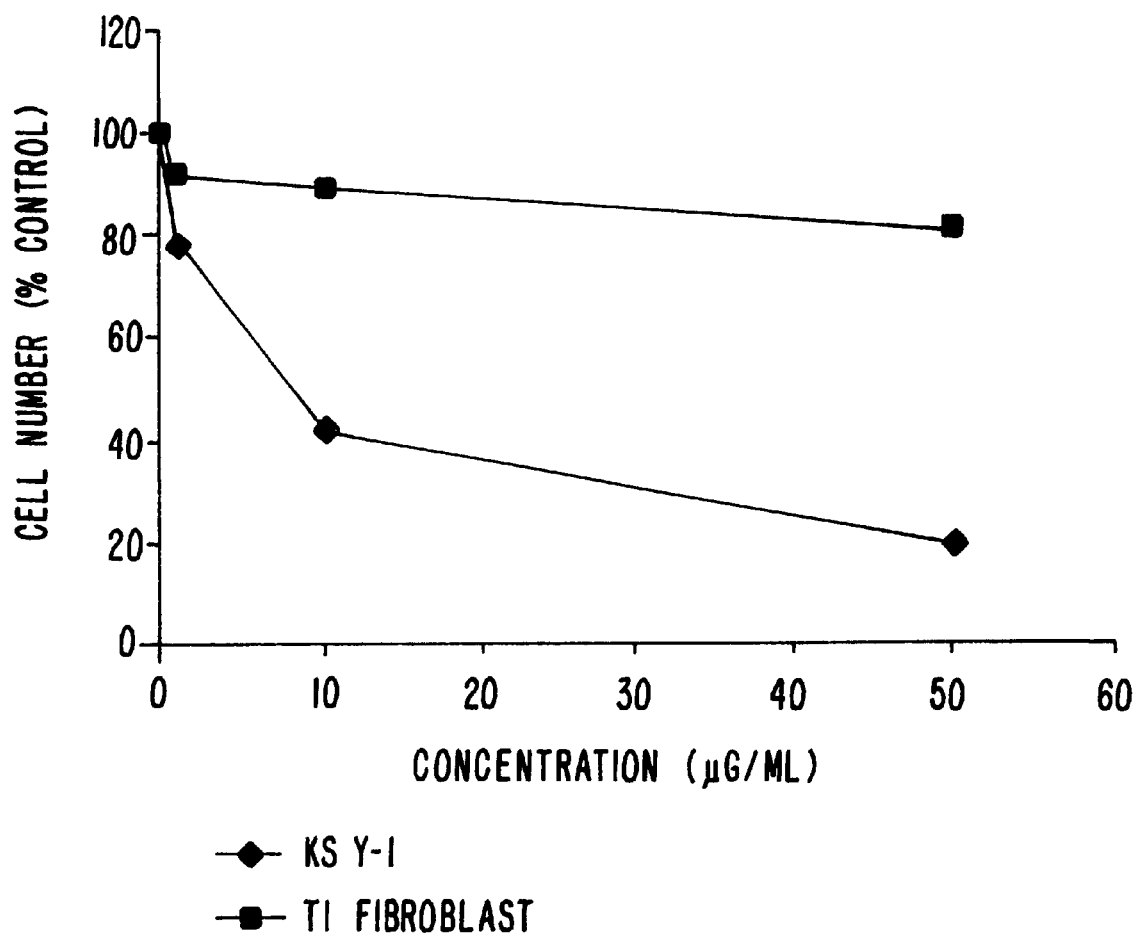
FIG. ID.

1

INHIBITORS OF ANGIOGENESIS AND TUMOR GROWTH

CROSS-REFERENCES TO RELATED APPLICATIONS

This Application is a continuation in part of U.S. Provisional Application No. 60/092,647, filed Jul. 13, 1998, which is incorporated by reference in its entirety.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

Angiogenesis is the formation of new blood vessels from existing blood vessels. To initiate the angiogenic process, biochemical signals stimulate protease secretion from, among other cell types, endothelial cells lining the lumen of the vessel. The secreted proteases degrade the basement membrane and the endothelial cell layer protrudes through the hole created in the basement membrane. If the biochemical signals are continuously present, the migrating endothelial cells undergo mitosis and divide. The dividing cells form a sprout through the vessel wall. Again, if the angiogenic stimulus remains, the sprouts merge to form capillary loops which later mature into new blood vessels.

Under normal circumstances of wound healing, fetal and embryonic development and formation of the corpus luteum, endometrium and placenta, the initial angiogenic signals subside and other, secondary, signals predominate to turn off the angiogenic process. However in disease states such as cancer, angiofibroma, neovascular glaucoma, arteriovenous malformations, nonunion fractures, arthritis and other connective tissue disorders, Osler-Weber syndrome, atherosclerotic plaques, psoriasis, corneal graft neovascularization, pyogenic granuloma, retrolental fibroplasia, diabetic retinopathy, scleroderma, hemangioma, trachoma, vascular adhesions and hypertrophic scars, the local concentration of angiogenic signals never decreases and new blood vessels continuously form, supplying the diseased tissue with nutrients. This allows the tumor or diseased tissue to grow.

In cancer, undesired angiogenesis provides a steady supply of nutrients to the tumor. This allows the tumor to grow as well as metastasize. However, in addition to a general tumor growth-supporting role, some tumors are highly angiogenic. For example, Kaposi's Sarcoma (KS) is a tumor characterized by unregulated growth of blood vessels. It is, in fact, an angiogenic tumor. Currently, the treatment of Kaposi's Sarcoma, like most tumors, is based on chemotherapy. However, most chemotherapeutic agents are universally harmful to all dividing cells; cancerous or not. Thus, there is a need for compounds that will reduce the angiogenesis required for many disease states, including cancer and specifically, Kaposi's Sarcoma. This invention surprising meets these and other needs.

BRIEF SUMMARY OF THE INVENTION

A surprising discovery of this invention is that Saposin B, previously known as a protein involved in the hydrolysis of sphingolipids has potent anti-angiogenic and antitumoral activity. In addition, this protein has been found to have anti-proliferative and anti-migratory activity against endothelial cells. Even more surprising was the discovery that the activity against tumor and endothelial cells was conserved in cryptic polypeptides as small as five amino acids. These small polypeptides can now be used either in vitro as well as in vivo as anti-angiogenic and anti-tumor agents.

One embodiment of this invention is an isolated polypeptide of about 5 to about 80 amino acids in length and comprising a contiguous amino acid sequence $DX_1CX_2D$. $X_1$ and $X_2$ can be any amino acid. In one aspect of this embodiment, the isolated polypeptide is between 7 and 50 amino acids in length. In another embodiment, the isolated polypeptide is between 11 and 50 amino acids in length. In yet another embodiment, the isolated polypeptide is between 5 and 40 amino acids in length. In yet another embodiment, the isolated polypeptide is between 7 and 40 amino acids in length. In yet another embodiment, the isolated polypeptide is between 11 and 40 amino acids in length. In yet another embodiment, the isolated polypeptide is between 5 and 30 amino acids in length. In yet another embodiment, the isolated polypeptide is between 7 and 30 amino acids in length. In yet another embodiment, the isolated polypeptide is between 11 and 30 amino acids in length. In yet another embodiment, the isolated polypeptide is between 5 and 20 amino acids in length. In yet another embodiment, he isolated polypeptide is between 7 and 20 amino acids in length. In yet another embodiment, the isolated polypeptide is between 11 and 20 amino acids in length.

In further embodiments, $X_1$ is a valine or a conservatively modified variant thereof or $X_2$ is a glutamine or a conservatively modified variant thereof. In a preferred embodiment, the polypeptide will comprise the contiguous amino acid sequence DVCQD (SEQ ID NO:28).

In yet another embodiment, the isolated polypeptide specifically binds to an antibody raised against Saposin B. In a preferred embodiment, the polypeptide comprises an amino acid sequence substantially identical to that shown in SEQ ID NO:2 beginning at position 2. In a most preferred embodiment, the polypeptide comprises at least 5 contiguous amino acids, or conservatively modified variants thereof, said contiguous amino acids having an amino acid sequence as shown in SEQ ID NO:2, beginning at position 2.

In still another embodiment, the isolated polypeptide comprises R-DVCQD-R'; wherein R is from 0 to about 6 contiguous amino acids; and wherein R' is from 0 to about 59 contiguous amino acids (SEQ ID NO:49). In a preferred embodiment, the polypeptide comprises R-XDVCQD-R'; wherein R is selected from the group consisting of $Aa_1$-$Aa_2$-$Aa_3$-$Aa_4$-$Aa_5$, $Aa_2$-$Aa_3$-$Aa_4$-$Aa_5$, $Aa_3$-$Aa_4$-$Aa_5$, $Aa_4$-$Aa_5$ and $Aa_5$. $Aa_1$, $Aa_2$, $Aa_3$, $Aa_4$ and $Aa_5$ or no amino acid are selected from the group consisting of amino acids; X is selected from the group consisting of G, A, S and T; and wherein R' is from 0 to about 59 contiguous amino (SEQ ID NO:45) acids. In a more preferred embodiment (SEQ ID NO:46), $Aa_1$ is a glutamine or a conservative substitution thereof, $Aa_2$ in a proline or a conservative substitution thereof, $Aa_3$ in a lysine or a conservative substitution thereof, $Aa_4$ in an aspartic acid or a conservative substitution thereof, or $Aa_5$ in a asparagine or a conservative substitution thereof.

In another embodiment, R' is selected from the group consisting of $Aa_{12}$-$Aa_{13}$-$Aa_{14}$-$Aa_{15}$-$Aa_{16}$, $Aa_{12}$-$Aa_{13}$-$Aa_{14}$-$Aa_{15}$, $Aa_{12}$-$Aa_{13}$-$Aa_{14}$, $Aa_{12}$-$Aa_{13}$ and $Aa_{12}$, or no amino acid, wherein $Aa_{12}$, $Aa_{13}$, $Aa_{14}$, $Aa_{15}$ and $Aa_{16}$ are selected from the group consisting of amino acids (SEQ ID NO:47). In a preferred embodiment (SEQ ID NO:48), $Aa_{12}$ is a cysteine or a conservative substitution thereof, $Aa_{13}$ is an isoleucine or a conservative substitution thereof, $Aa_{14}$ is an glutamine or a conservative substitution thereof, $Aa_{15}$ is a methionine or a conservative substitution thereof, or $Aa_{16}$ is a valine or a conservative substitution thereof.

In a most preferred embodiment, the isolated polypeptide has the amino acid sequence GDVCQDCIQMV (SEQ ID NO:19).

In another embodiment of this invention, a receptor is provided wherein the receptor specifically binds to Saposin B and is found on the surface of cells selected from the group consisting of KS Y-1, SLK, HUVEC and murine endothelial cells. In a preferred embodiment, the receptor is recombinantly expressed.

In another embodiment, a method of treating a mammal is provided, wherein said organism has a pathological condition associated with undesired angiogenesis. The method comprises administering to the mammal an amount of an isolated polypeptide comprising a contiguous amino acid sequence $DX_1CX_2D$, wherein $X_1$ and $X_2$ are selected from the group consisting of amino acids, wherein the amount of polypeptide effective to reduce angiogenesis. In a most preferred embodiment, the mammal is human and the isolated polypeptide is Saposin B.

In a more preferred embodiment, the pathological condition to be treated is cancer. In the most preferred embodiment, the cancer is Kaposi's Sarcoma. Administration of the isolated polypeptide is selected from the group consisting of subcutaneous, intramuscular, intravenous, intra-arterial, intrabronchial, parenteral, transdermal, intraocular, rectal, vaginal, intranasal, sublingual and intralesional. In the most preferred embodiment, the administration is selected from the group consisting of intralesional and transdermal.

In yet another embodiment, a pharmaceutical composition in unit dosage form is provided, the composition comprising one or more pharmaceutically acceptable excipients, and an amount of a polypeptide comprising a contiguous amino acid sequence $DX_1CX_2D$, wherein $X_1$ and $X_2$ are selected from the group consisting of amino acids. The polypeptide is effective to treat or prevent undesired angiogenesis in an animal or patient to whom one or more unit doses of said composition are administered. In this embodiment, it is preferred the unit dosage form be a solution comprising said polypeptide.

In still another embodiment, a fusion protein is provided, wherein the fusion protein comprises a polypeptide of a contiguous amino acid sequence $DX_1CX_2D$, wherein $X_1$ and $X_2$ are selected from the group consisting of amino acids. The second moiety of the fusion protein is a cell targeting moiety. The cell targeting moiety and the polypeptide have functional activity independent of each other. In a more preferred embodiment, the cell targeting moiety is a protein. In a most preferred embodiment, the protein is an antibody. In a further refinement, the antibody is a monoclonal antibody. In yet another refinement, the antibody is a single chain Fv antibody.

In one embodiment of this invention, another fusion protein is provided, wherein the fusion protein comprises a polypeptide of a contiguous amino acid sequence $DX_1CX_2D$, wherein $X_1$ and $X_2$ are selected from the group consisting of amino acids. The fusion protein also comprises a cytotoxic moiety. The cytotoxic moiety and said polypeptide have functional activity independent of each other. In a preferred embodiment, the cytotoxic moiety is a protein. In a more preferred embodiment, the protein is a bacterial toxin. In a most preferred embodiment, the bacterial toxin is from Diphtheria, particularly the B chain of Diptheria toxin.

In a related embodiment, the bacterial toxin is from Pseudomonas, in particular Pseudomonas exotoxin. In the most preferred of this embodiment, the Pseudomonas exotoxin is selected from the group consisting of recombinant PE38 and PE40.

BRIEF DESCRIPTION OF THE FIGURES

FIG. 1D: Activity of n-terminus decapeptide (DVCQDCIQMV; SEQ ID NO 21). Only endothelial cells show dose dependent growth inhibition.

DEFINITIONS

Figure 1:
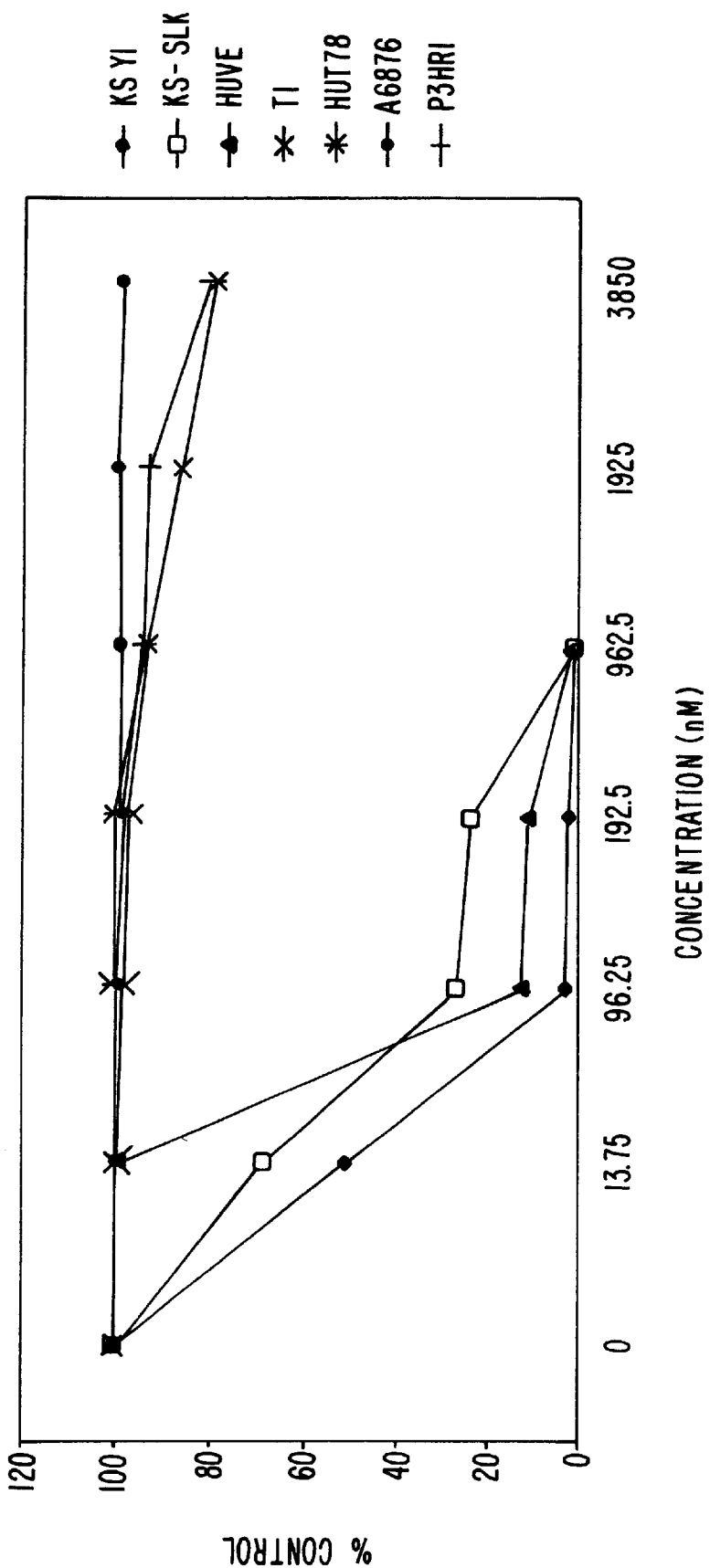
FIG. 1: Activity of recombinant Saposin B. Only KS and endothelial cells showed dose dependent growth inhibition.
Figure 1B:
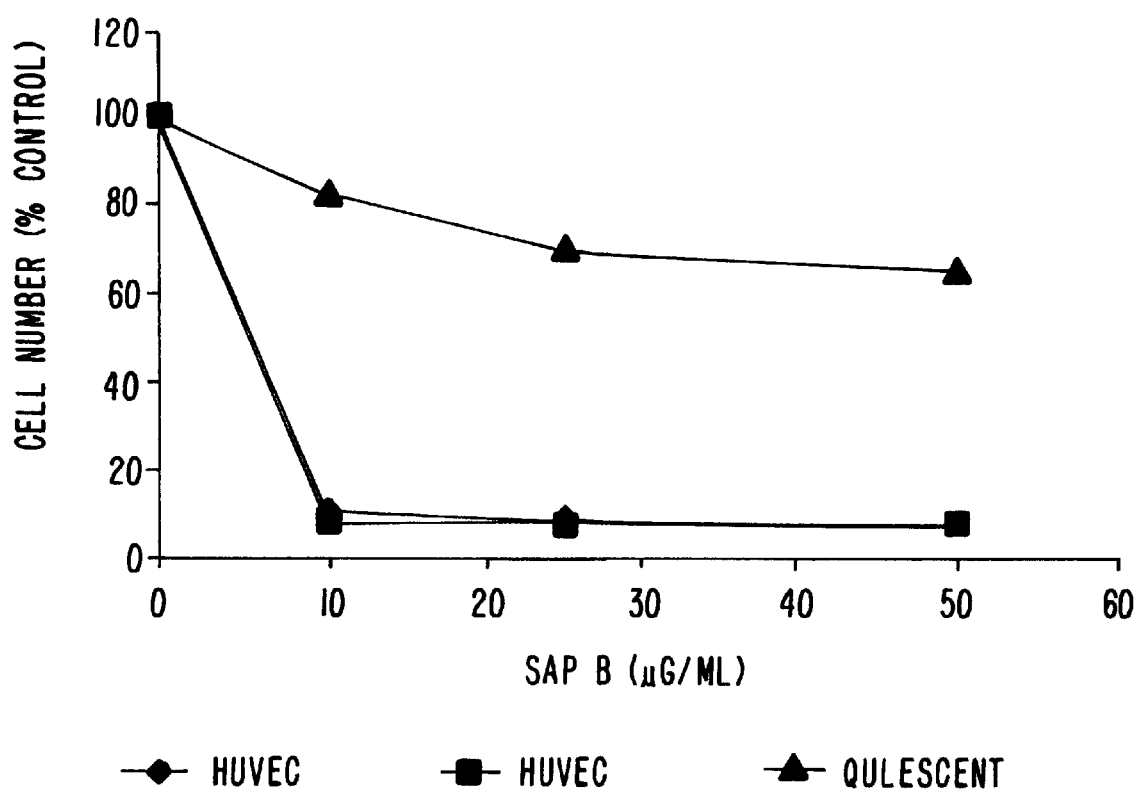
FIG. 1B: Activity of recombinant Saposin B. Only proliferating and not quiescent endothelial cells (HUVEC) show dose dependent growth inhibition.
Figure 1C:
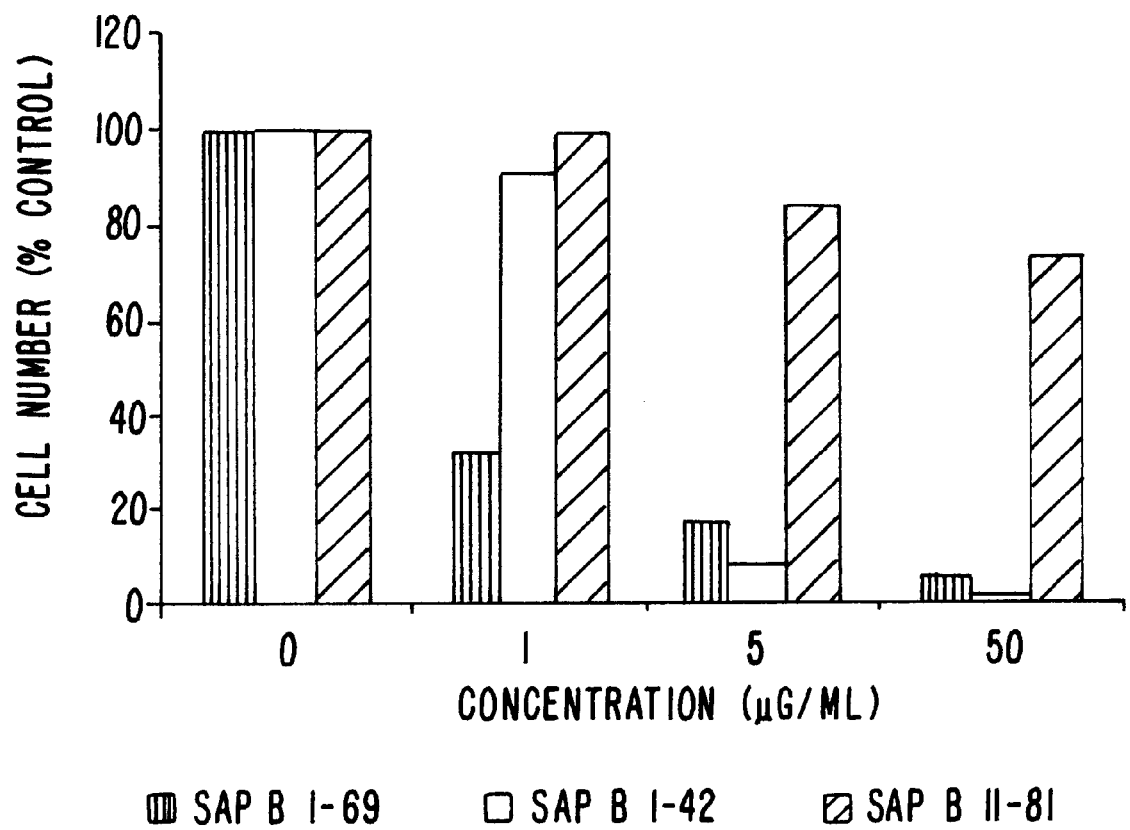
FIG. 1C: Activity of truncated recombinant Saposin B. Saposin (Sap) B 1–69 (consisting of the first 69 amino acids), Sap B 1–42 (consisting of the first 42 amino acids), Sap B 11–81 (consisting of 11–81 amino acids and thus lacking the first 10 amino acids). Notably, Sap B 1–69 and Sap B 1–42, but not Sap B 11–81 showed dose dependent growth inhibition.
Figure 1E:
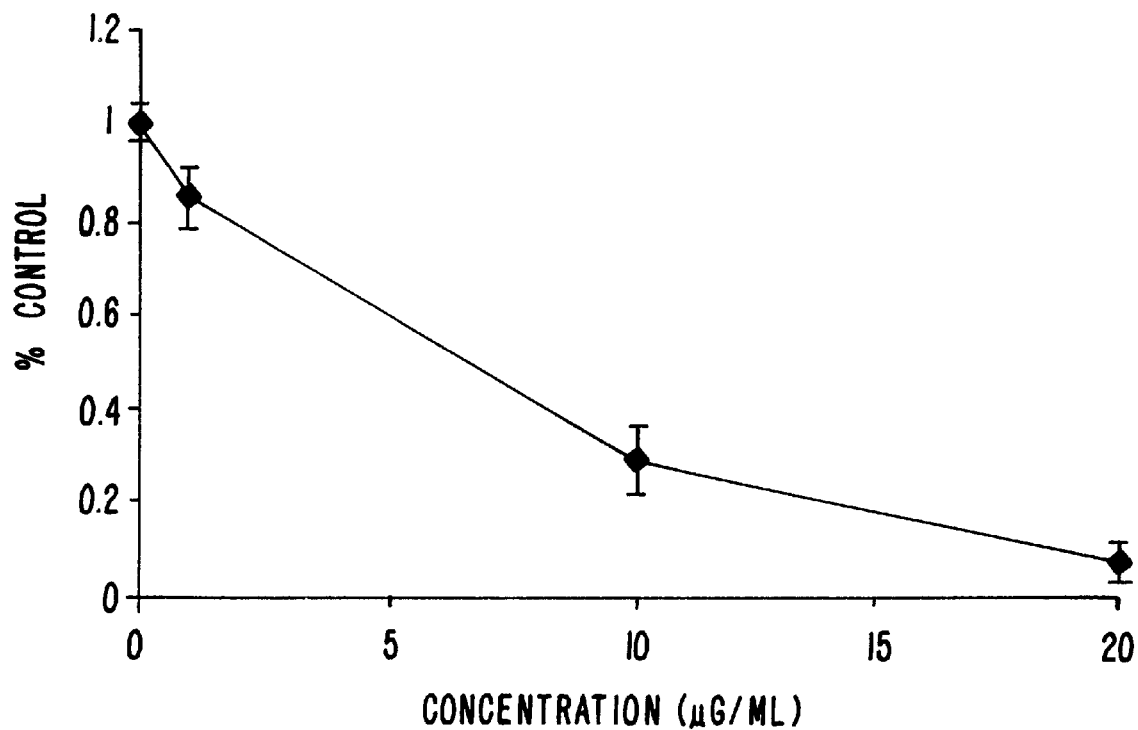
FIG. 1E: Activity of N-terminus pentapeptide (DVCQC; SEQ ID NO: 28). Only endothelial cells show dose dependent growth inhibition.
Figure 2A:
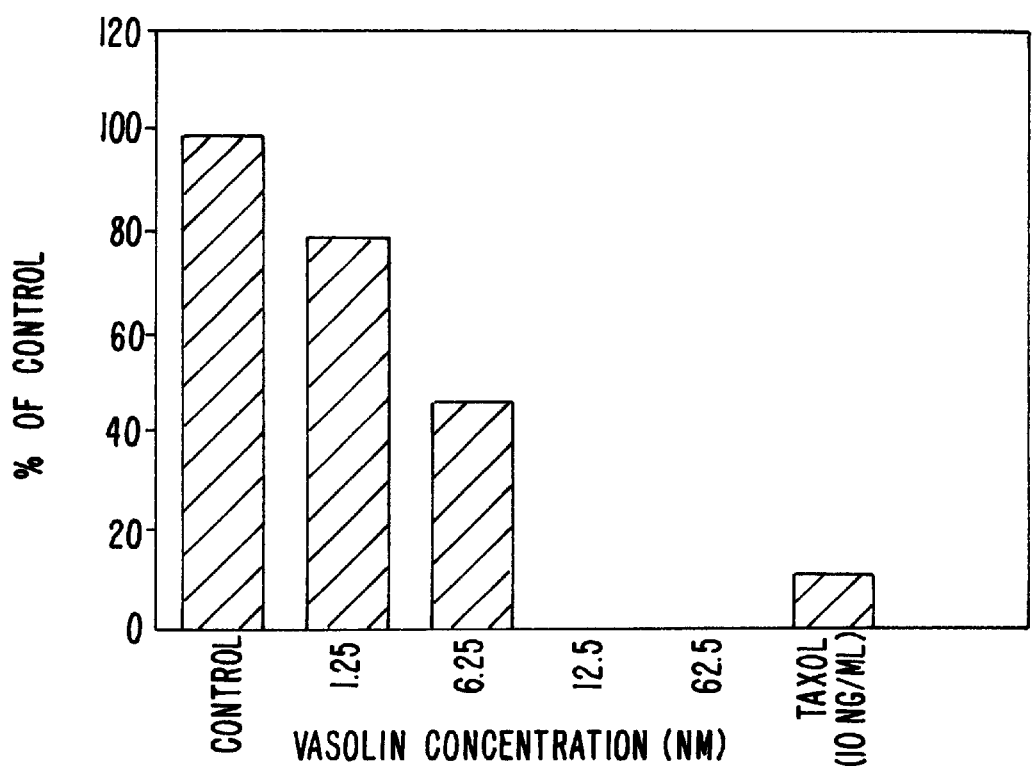
FIG. 2: Saposin B inhibited endothelial cell migration. The assays were done in double chamber wells separated by fibrinogen-coated membrane. Chemotaxis was induced by bFGF (25 ng/mL) in the lower chamber. Endothelial cells or KS cells ($5\times10^4$/mL) were placed in the upper chamber in the presence and absence of test polypeptides. Taxol at 10 ng/mL was used as a known inhibitor of migration. Cell migration across the membrane was quantitated after an overnight incubation.
Figure 2B:
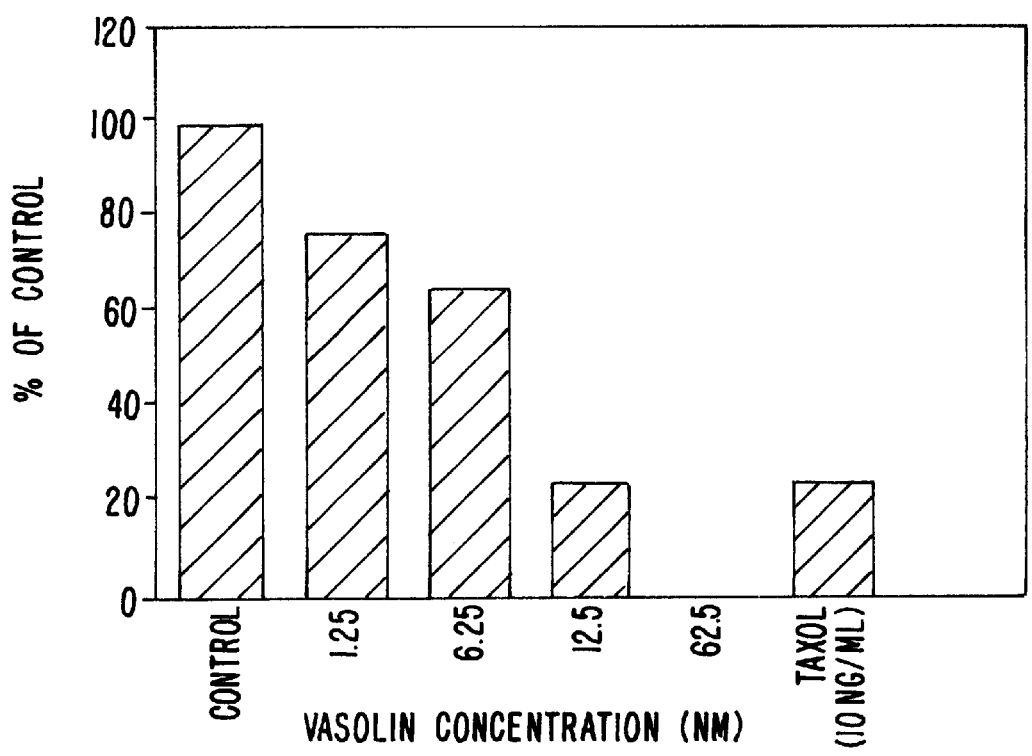
Figure 2C:
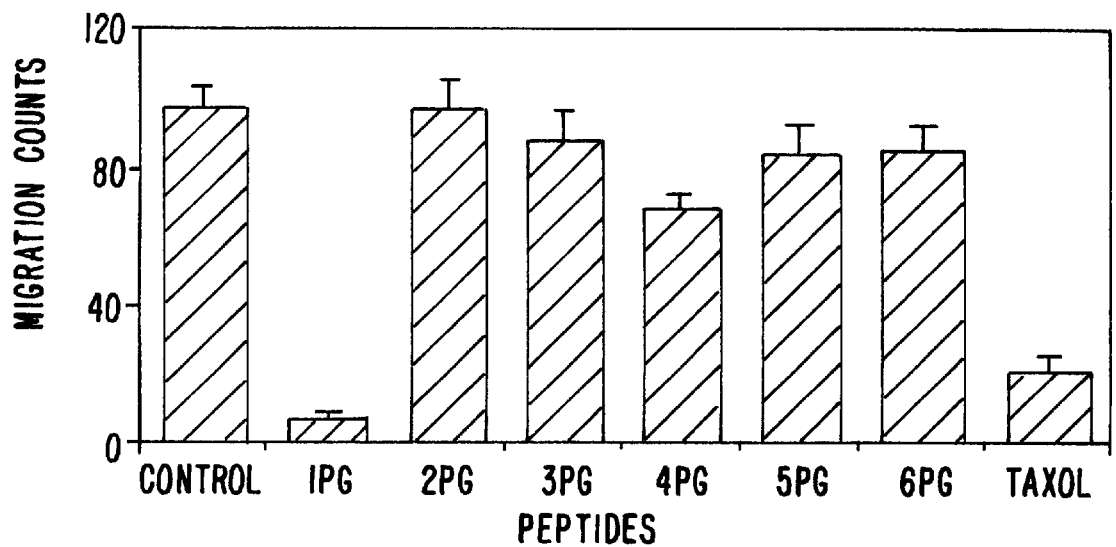
Figure 2D:
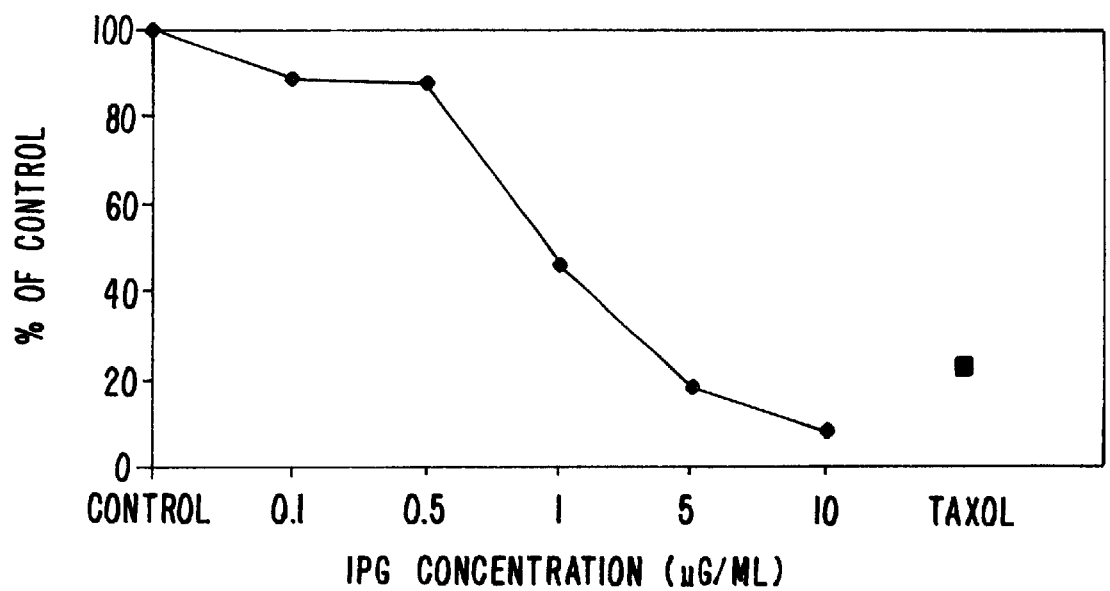

Unless defined otherwise herein, all technical and scientific terms used herein have the same meaning as commonly understood by one of ordinary skill in the art to which this invention belongs. Singleton, et al., *Dictionary of Microbiology and Molecular Biology*, 2d Ed., John Wiley and Sons, New York (1994), and Hale & Marham, *The Harper Collins Dictionary of Biology*, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxyl orientation, respectively. The headings provided herein are not limitations of the various aspects or embodiments of the invention which can be had by reference to the specification as a whole. Accordingly, the terms defined immediately below are more fully defined by reference to the specification as a whole.

The phrase "administering a therapeutic amount" refers to the means by which anti-angiogenic polypeptides are used to treat a mammal. The term "administering" is intended to encompass all methods which result in the contact between a mammal and the polypeptides of this invention, including but not limited to, subcutaneous, intramuscular, intravenous, intra-arterial, intraocular and intralesional injections; intra-bronchial and intranasal inhalation or instillation; rectal and vaginal suppositories; sublingual and oral delivery; and absorption across the dermal and mucosal barriers.

The term "amino acid" includes reference to an amino acid that is incorporated into a protein, polypeptide, or peptide (collectively "polypeptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table 1:

TABLE 1

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Unless stated otherwise, "$X_n$" and "$Aa_n$" refer to any amino acid. The amino acid may be a naturally occurring L-amino acid, a D-amino acid or any synthetic amino acid analog. The phrase "contiguous amino acid sequence" refers to a linear amino acid sequence wherein the first amino acid is at the N terminus of the polypeptide and the last amino acid is at the C terminus. The terms "R" and "R'" refer to contiguous amino acid sequences. Unless stated otherwise, "R" is a contiguous amino acid sequence at the N terminus of a polypeptide and "R'" is a contiguous amino acid sequence at the C terminus of a polypeptide. R and R' do not necessarily comprise the same contiguous amino acid sequence.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), or disulfide stabilized (dsFv) Fv fragments (see, U.S. Pat. No. 5,747,654). The term "antibody" also includes antigen binding forms of antibodies (e.g., Fab', F(ab')$_2$, Fab, Fv and rIgG. See also, Pierce Catalog and Handbook, 1994–1995 (Pierce Chemical Co., Rockford, Ill.)).

An antibody immunologically reactive with a particular antigen can be generated by recombinant methods such as selection of libraries of recombinant antibodies in phage or similar vectors. See, e.g., Huse, et al., *Science* 246:1275–1281 (1989); Ward, et al., *Nature* 341:544–546 (1989); and Vaughan, et al., *Nature Biotech.* 14:309–314 (1996).

Typically, an immunoglobulin has a heavy and light chain. Each heavy and light chain contains a constant region and a variable region. Light and heavy chain variable regions contain a "framework" region interrupted by three hypervariable regions, also called complementarity-determining regions or CDRs. The extent of the framework region and CDRs have been defined (see, *Sequences of Proteins of Immunological Interest*, Kabat, E., et al., U.S. Department of Health and Human Services, (1987)). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site. A "linker peptide" includes, but is not limited to, peptides within an antibody binding fragment (e.g., Fv fragment) which serve to indirectly bond the variable heavy chain to the variable light chain.

The phrase "aseptic solution" refers to a solution that is microorganism-free. Making a solution microorganism-free can be done by removal of or by killing the microorganisms. Methods of removal of microorganisms consist primarily of filtration using a membrane with a pore size smaller than the microorganism. Typically, the pore size is 0.11–0.22 μm. Another, less preferred method of removing microorganisms is by centrifugation. Methods of killing microorganisms are well known in the art and include but are not limited to, pasteurization, treatment with high pressure and temperature, i.e., autoclaving, contact with anti-microbial agents, e.g., antibiotics, antivirals, antifungals, etc. However, one of skill will realize that in some embodiments of this invention, the solutions are intended to be administered to mammals in need of treatment. Therefore, the agents used to kill microorganisms should not have adverse effects on the mammal to be treated.

The term "cancer", for purposes of this disclosure, refers to a pathological condition caused by unregulated in vivo growth of cells. Thus, for purposes of this disclosure, cancer includes but is not limited to the following: solid as well as hematopoietic tumors, malignant and benign tumors, primary and metastatic tumors, and precancerous conditions. One such cancer is "Kaposi's Sarcoma." Kaposi's Sarcoma presents in three different classes of individuals. Classic Kaposi's sarcoma is a rare, indolent, cancer of mainly elderly men of Jewish or Mediterranean origin (Lospalleti, M., et al., *Dermatology* 191(2): 104–8 (1995)). Endemic Kaposi's Sarcoma (EKS) affects elderly and young Africans, particularly Bantus. EKS can become particularly aggressive after a long period of quiescence (Safai, B., *Semin Oncol* 2 (Suppl 3): 7–12 (1987)). HIV-associated Kaposi's sarcoma is an aggressive cancer found as an opportunistic disease related to infection with HIV (Wahman, A., et al., *Epidemiol Rev.* 13:178–9 (1991)). In all of the above types of Kaposi's sarcoma, a compromised immune system is indicated.

The HIV-related form of Kaposi's sarcoma (AIDS-KS) most frequently presents with cutaneous lesions. Occasionally, cases present with lymph node or visceral KS only. Mucosal involvement of the oral cavity is the second most common site of disease. The tumor lesions are noted frequently on the palate, gums and can cause tooth loss, pain and ulceration (Paredes, J., *J. Acquir. Immune Defic. Syndr. Hum. Refroviral* 9(2):138–44 (1995)).

A "conservative substitution," when describing a polypeptide refers to a change in the amino acid composition of the polypeptide that does not substantially alter the polypeptide's activity. "Conservatively modified variations" of a particular amino acid sequence refers to amino acid substitutions of those amino acids that are not critical for functional activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art.

A "cell targeting moiety," as used herein, refers generally to compounds capable of specifically delivering a molecule, reacting with or otherwise recognizing or binding to a target cell. Specifically, examples of cell targeting moieties include, but are not limited to, immunoglobulins or binding fragments thereof, lymphokines, cytokines, cell surface antigens, solubilized receptor proteins, hormones, growth factors such as epidermal growth factor (EGF), and the like which specifically bind desired target cells. Although the above exemplified cell targeting moieties are polypeptides, it is not necessary that cell targeting moieties consist of polypeptides. Cell targeting moieties can also be carbohydrates, drugs, lipids or any other compound which selectively binds to a target cell.

The term "cytotoxic moiety" includes, but is not limited to, abrin, ricin, Pseudomonas exotoxin (PE), diphtheria toxin (DT), botulinum toxin, or modified toxins thereof. For example, PE and DT are bacterial toxins that typically bring about death through liver toxicity. PE and DT, however, can be modified into a form for use in a fusion protein by removing the native targeting component of the toxin (e.g., domain Ia of PE and the B chain of DT) and replacing it with a different moiety, such as a polypeptide which specifically binds to a cell to be killed. "PE38" and "PE40" refer to a 38 kD and a 40 kD, respectively, cytotoxic moiety derived from PE. See, for example, U.S. Pat. Nos. 5,082,927 and 5,696, 237 as well as Chaudhary, et al., *Nature* 339:394 (1989) for descriptions of and methods of making and using PE40 and Chaudhary, et al., *Proc. Nat'l Acad. Sci. USA* 87:308 (1990) and Benhar, et al., *Bioconjug. Chem.* 5:321 (1994) for descriptions of PE 38 as well as methods for making and using PE38.

The terms "effective amount" or "amount effective to" or "therapeutically effective amount" includes reference to a dosage of a therapeutic agent sufficient to produce a desired result, such as inhibiting the formation of new blood vessels by at least 25%, or killing a cell.

The phrase "functional activity independent of each other", in the context of this invention, refers to the activity of the two moieties of the fusion proteins of this invention. For example, the polypeptides of the fusion proteins have anti-angiogenic activity. This activity is independent of the cell targeting or cytotoxic activity of the other moiety of the fusion protein.

A "fusion protein" refers to a chimeric molecule formed by the joining of two or more compounds through a bond formed between one moiety and another moiety. For purposes of this invention, one moiety is a polypeptide. The bond between the polypeptide and the other moiety may be covalent or noncovalent. An example of a covalent bond is the chemical coupling of two polypeptides to form peptide bond. Examples of non-covalent bond are hydrogen bonds, electrostatic interactions and van der Waal's forces.

If the bond is a peptide bond and the other moiety is a polypeptide as well, the fusion protein may be expressed as a single polypeptide from a nucleic acid sequence encoding a single contiguous fusion protein.

The term "identical" in the context of two polypeptide sequences refers to the residues in the two sequences that are the same when aligned for maximum correspondence, as measured using one of the following "sequence comparison algorithms." The phrase "substantially identical" in the context of two polypeptides refers to the residues in the two sequences that have at least 60% identity when aligned for maximum correspondence over a domain of the protein. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendrogram or tree representation of clustering relationships. The program is run by designating specific sequences and their amino acid coordinates for regions of sequence comparison.

Another example of algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information.

This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul, et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to an ribonuclease nucleic acid if the smallest sum probability in a comparison of the test nucleic acid to an ribonuclease nucleic acid is less than about 0.1, more preferably less than about 0.01, and most preferably less than about 0.001. Where the test nucleic acid encodes a ribonuclease polypeptide, it is considered similar to a specified ribonuclease nucleic acid if the comparison results in a smallest sum probability of less than about 0.5, and more preferably less than about 0.2.

Another indication that two polypeptides are substantially identical is that the first polypeptide is immunologically cross-reactive with the second polypeptide. Thus, a polypeptide is substantially identical to a second polypeptide, for example, where the two peptides differ only by a conservative substitution.

The terms "isolated," "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A polypeptide that is the predominant species present in a preparation is substantially purified. The term "purified" denotes that a polypeptide gives rise to essentially one band in an electrophoretic gel. Particularly, it means that the polypeptide is at least 85% pure, more preferably at least 95% pure, and most preferably at least 99% pure.

The term "liposome" refers to vesicles comprised of one or more concentrically ordered lipid bilayers which encapsulate an aqueous interior. Normally, the encapsulated interior matrix does not permeate the bilayer. However, if a hole or pore occurs in the bilayer, if the bilayer is dissolved or degraded, if the bilayer changes conformation, or if the environmental temperature is increased to the phase transition temperature, Tc, of the constituent lipids, the matrix may leak through the liposome.

The "interior" of a liposome is the aqueous area surrounded by the lipid bi-layer of the liposome, i.e., encapsulated matrix. The process of placing a compound within the aqueous matrix is termed "encapsulating." The "surface" of a liposome is the hydrophilic portion of the substituent lipids exposed to the extraliposomal environment. Binding of a polypeptide to the interior or exterior surface of a liposome can be due to covalent bonding of the compound to the hydrophilic group, hydrogen bonding, electrostatic interactions, or hydrophobic/hydrophilic interactions. In addition to binding to the surface, a compound with a hydrophobic component can insert into the liposome bilayer so that the hydrophobic component is within the bilayer and the hydrophilic portion of the compound extends beyond the surface of the liposome or into the interior matrix of the liposome.

"Pharmaceutically acceptable excipients" refers to ingredients other than the active ingredient in the pharmaceutical compositions of this invention.

The phrase "pharmaceutical composition" refers to compositions of the polypeptides or fusion proteins of this invention mixed with suitable carriers or excipient(s) in a therapeutically effective amount, e.g., at doses effective to reduce angiogenesis.

As used herein, "polypeptide," "peptide" and "protein" are used interchangeably and include reference to a polymer of amino acid residues and/or amino acid analogs. The terms apply to amino acid polymers in which one or more amino acid residue is an artificial chemical analog of a corresponding naturally occurring amino acid, e.g., a peptidomimetic, as well as to naturally occurring amino acid polymers. The terms also apply to polymers containing conservative amino acid substitutions such that the polypeptide remains functional. The term polypeptide also includes concatemer units of a motif, or a contiguous amino acid sequence within a larger amino acid sequence, or polypeptides comprising the motif.

The phrase "antibody raised against Saposin B" refers to antibodies that can neutralize the anti-angiogenic activity of Sasposin B or of the active peptides provided herein. The antibodies can be either polyclonal or monoclonal. These antibodies are produced or raised by immunogenically exposing Saposin B to the immune system of an animal able to produce antibodies specific to Saposin B As used herein, "recombinant" includes reference to a polypeptide produced using cells that do not have, in their native state, an endogenous copy of the DNA able to express the polypeptide. The cells produce the recombinant polypeptide because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under expressed or not expressed at all.

The term "Saposin B" refers to a polypeptide fragment of Prosaposin. Prosaposin is a 70 kD glycoprotein which has been deposited and given GenBank Accession No. 337762. Prosaposin is the precursor of four small heat-stable sphingolipid-binding glycoproteins labeled Saposin A, Saposin B, Saposin C and Saposin D. In addition to binding sphingolipids, Saposin C has been found to have neurotrophic activity. This peptide and its functional activity is described in U.S. Pat. No. 5,696,080. Saposin B is associated with lysosomal hydrolysis of sphingolipids, including sulfatides, GM1 ganglioside, globotriaosylceramide. In addition to sphingolipids, Saposin B is involved in the hydrolysis of glycerolipids (Hiraiwa, et al., *Arch. Biochem. Biophys.* 303:326 (1993)). In reference to the deposited Prosaposin amino acid sequence, the Saposin B amino acid sequence resides between positions 190 and 269, inclusive. Humans with Saposin B deficiency have an accumulation of cerebroside sulfate and a clinical presentation of leukodystrophy (Kretz, et al., *Proc. Nat'l Acad. Sci. USA* 87:2541 (1990)). See also, Kase, et al., *FEBS Lett.* 393:74 (1996) and Lamontagne & Potier, *J. Biol. Chem.* 269:20528 (1994). In addition to its sphingolipid hydrolysis activity, Saposin B, as disclosed below, surprisingly has anti-angiogenic activity. Even more surprising, polypeptides of Saposin B, some as small as five amino acids, have anti-angiogenic activity.

The phrase "specifically (or selectively) binds" refers to a binding reaction that is determinative of the presence of a polypeptide in a heterogeneous population of polypeptides and other compounds. Thus, under designated binding conditions, the specified polypeptides bind to a particular compound at least two times the background and do not substantially bind in a significant amount to other compounds present in the sample. Specific binding to an antibody under such conditions may require an antibody that is selected for its specificity for a particular polypeptide. For example, antibodies raised to a polypeptide of this invention can be selected so that a composition of antibodies will comprise only antibodies that are specifically immunoreactive with the polypeptides and not with other compounds, except for polymorphic variants, alleles, and closely related interspecies homologs of the polypeptides. This selection may be achieved by subtracting out antibodies that cross-react with other polypeptides, for example, Saposin C.

The phrase "surface of cells" refers to the interstitial aspect of a cellular membrane. In some cases, the surface of a cell will comprise a compound that is embedded in the membrane and has an extracellular component that is available for binding to compounds in the interstitium.

The term "therapeutic agent" includes any number of compounds which will be apparent to one of skill upon review of this disclosure that act as anti-neoplastics, anti-angiogenics or other agents administered to induce a desired therapeutic effect in a patient.

The phrase "treating an mammal" refers to administering a polypeptide or a fusion protein of this invention to a mammal in order to obtain a desired result, ie., decrease undesired angiogenesis.

"Undesired angiogenesis" refers to uncontrolled persistent angiogenesis, or unregulated growth of capillary loops and blood vessels, occurring in tumor growth, tumor metastasis, and abnormal endothelial growth among other pathological conditions. The phrase "reduce angiogenesis" refers to decreasing the undesired formation of capillary loops and blood vessels. One of skill will realize that although reduction of undesired angiogenesis is desired, reduction of desired angiogenesis, i.e., normal growth of capillary loops and blood vessels, may also be reduced.

The phrase "unit dosage form" refers essentially to the final composition form, e.g., the capsules; tablets; suppositories; solutions; powders, both lyophilized and admixed; impregnated transdermal patches; vials and the like into which the composition is ultimately delivered to the marketplace.

SEQUENCE LISTING

In the Sequence Listing, SEQ ID NO:2 corresponds to the amino acid sequence of Saposin B. At position 2 of this amino acid sequence is an aspartic acid residue. SEQ ID NO:1 is the amino acid sequence of full length Prosaposin. SEQ ID NOS:3 and 4 are nucleic acid primers used to amplify the nucleic acid sequence which encodes Saposin B. SEQ ID NOS:5 and 6 are nucleic acid primers used to amplify the nucleic acid sequence which encodes Prosaposin. SEQ ID NOS:7 and 8 are nucleic acid primers used to amplify the nucleic acid sequence which encodes Saposin A. SEQ ID NOS: 9 and 10 are nucleic acid primers used to amplify the nucleic acid sequence which encodes Saposin C. SEQ ID NOS: 10 and 11 are nucleic acid primers used to amplify the nucleic acid sequence which encodes Saposin D.

The amino acid sequence of human prosaposin (SEQ ID NO:1). The sequence of Saposin B mature peptide (SEQ ID NO:2) is indicated in underlined bold lettering.

MYALFLLASLLGAALAGPVLGLKECTRGSAVWC
QNVKTASDCGAVKHCLQTVWNKPTVKSLPCDIC
KDVVTAAGDMLKDNATEEEILVYLEKTCDWLPK
PNMSASCKEIVDSYLPVILDIIKGEMSRPGEVCSAL
NLCESLQKHLAELNHQKQLESNKIPELDMTEVV
APFMANIPLLLYPQDGPRSKPQPKDN**GDVCODCIOM
VTDIOTAVRTNSTFVQALVEHVK E E C D R L G P M A
DICKNYISQYSEIAIQMMMHMQPKEICALVGFCDEVK**
EMPMQTLVPAKVASKNVIPALELVEPIKKHEVPAKS
DVYCEVCEFLVKEVTKLIDNNKTEKEILDAFDKMCS
KLPKSLSEECQEVVDTYGSSILSILLEEVSPELVCS
MLHLCSGTRLPALTVHVTQPKDGGFCEVCKKLV
GYLDRNLEKNSTKQEILAALEKGCSFLPDPYQK
QCDQFVAEYEPVLIEILVEVMDPSFVCLKIGACPSAH
KPLLGTEKCIWGPSYWCQNTETAAQCNAVEHC
KRHVWN

Table 2 provides sequences that are anti-angiogenic polypeptides of this invention.

TABLE 2

Anti-angiogenic Polypeptides

| SEQ ID NO: | Amino Acid Sequence |
| --- | --- |
| 13 | QPKDNGDVCQDCIQV |
| 14 | IQMVTDIQTAVRTNSTF |
| 15 | STFVQALVEHVKEECDR |
| 16 | CDRLGPGMADKNYS |
| 17 | YISQYSEIAIQMMMHMQP |
| 18 | QMMMHMQPKEICALVG |
| 19 | GDVCQDCIQMV |
| 20 | GDVSQDSIQMV |
| 21 | DVCQDCIQMV |
| 22 | GDVCQ |
| 23 | DCIQMV |
| 24 | DVCQDCIQM |
| 25 | DVCQDCIQ |

TABLE 2-continued

Anti-angiogenic Polypeptides

| SEQ ID NO: | Amino Acid Sequence |
|---|---|
| 26 | DVCQDCI |
| 27 | DVCQDC |
| 28 | DVCQD |
| 29 | VCQDCIQMV |
| 30 | CQDCIQMV |
| 31 | QDCIQMV |
| 32 | GDVSQDCIQMV |
| 33 | GDVCQDSIQMV |
| 34 | GDVSQD |
| 35 | DACQD |
| 36 | DICQD |
| 37 | DLCQD |
| 38 | DVCSD |
| 39 | DVCED |
| 40 | DVCDD |
| 41 | QPKEICALVGFCDEVK |
| 42 | CDRLGPGMAKICKNYIS |
| 43 | QMVTDIQTQVRTNSTF |

DETAILED DESCRIPTION OF THE INVENTION

This invention is directed towards polypeptides which possess anti-angiogenic properties as well as anti-tumoral properties. The polypeptides described herein include cryptic as well as N-terminal peptides of Saposin B and the full-length Saposin B, a protein heretofore only known to have activity associated with the hydrolysis of sphingolipids and phosphoglycerides. Saposin B is highly conserved and this invention includes corresponding proteins and peptides from humans as well as other animal species including mice, rats, chickens, dogs and primates.

The polypeptides of this invention have a variety of uses. For example, they can be used as a therapeutic agent to treat undesired angiogenesis and tumor growth. In addition, because of their effect on specific cell types, the polypeptides of this invention can be used in conjunction with cell cytotoxic moieties to selectively kill certain cell types. The polypeptides can also be linked to cell targeting moieties to modulate cells upon which the polypeptide would not normally be active. In addition to in vitro uses, the polypeptides of this invention can also be used in vitro. For example, the polypeptides can be used to generate antibodies which then can be used to treat diseases caused by an overproduction of Saposin B or Prosaposin. In another example, the polypeptides can be used to generate synthetic drugs with similar activity.

The diseases and pathological conditions for which the compounds and methods of this invention include, but are not limited to, cancer, angiofibroma, neovascular glaucoma, arteriovenous malformations, nonunion fractures, arthritis and other connective tissue disorders, Osler-Weber syndrome, atherosclerotic plaques, psoriasis, corneal graft neovascularization, pyogenic granuloma, retrolental fibroplasia, diabetic retinopathy, scleroderma, hemangioma, trachoma, vascular adhesions and hypertrophic scars. One of skill, upon review of this disclosure, will appreciate that other diseases states and pathological conditions are susceptible to treatment with the compounds and methods of this invention as well.

The diseases treatable with Saposin B and its derivative peptides include human as well as veterinary uses such as treating cats, dogs, horses and cattle.

I. Polypeptides and Fusion Proteins of this Invention

A. Sources of the Polypeptides and Fusion Proteins

1. Natural Sources of the Polypeptides

The polypeptides of this invention can be obtained from natural sources. Natural sources in this context comprises mammals including, but not limited to, humans. In a preferred embodiment, the polypeptides of this invention are isolated from the body fluids of humans. In a particularly preferred embodiment, the body fluid is urine. In this embodiment, the preferred polypeptide is Saposin B (SEQ ID NO:2).

One of skill in the art will realize that, because of the inherent danger of processing body fluids, care should be taken to avoid contact with the fluid during collection and preparation of the polypeptides of this invention. During the collection period, the urine is preferable stored frozen. After a suitable amount has been collected, the urine is concentrated and fractionated.

Before concentration, the urine is thawed and centrifuged to remove solids. Typical centrifuge conditions are 800×g for 20 minutes at 4° C. To remove the remaining solids from the supernatant, the urine is preferably filtered through a 0.43 μm or another suitable filtration membrane. To concentrate the clarified urine, it can be precipitated with a compound that reduces the solubility of proteins in the urine, e.g., ammonium sulfate or polyethylene glycol. Alternatively, the urine can be filtered through a membrane in which the molecular weight cut off is less than the size of the desired polypeptide and therefore is retained, i.e., 2–5 kD. Examples of these filtration techniques include, but are not limited to, ultrafiltration and diafiltration, both of which are well known to those of skill in the art.

After the initial concentration step, the urine is fractionated on the basis of size by applying it to a size exclusion column. Because the polypeptides of this invention are a small fraction of the total protein found in urine, the absorbance at 280 nm is not sufficient to determine the presence of the polypeptides. Therefore, the functional and immunoassays described below preferably are used to determine which fractions contain anti-angiogenic polypeptides. If desired, an additional fractionation step, e.g., ion exchange, affinity and hydrophobic interaction chromatography, can be performed to further purify and/or concentrate the polypeptides. Again, these techniques are well known in the art.

To produce fusion proteins, another embodiment of this invention, the polypeptides are linked to a cell targeting or a cytotoxic moiety ("functional moiety"). The moieties can either be proteinaceous or another compound that has cell targeting or cytotoxic activity. The linkage between the polypeptide and the cell targeting or cytotoxic moiety is produced through chemical conjugation and is described in greater detail below.

Chemical modifications before chemical conjugation can be effected. These modifications include, for example, derivitization for the purpose of linking the polypeptide to the functional moiety, either directly or through a linking compound, by methods that are well known in the art of protein chemistry. In one preferred chemical conjugation embodiment, the means of linking the polypeptide and the functional moiety comprises a heterobifunctional coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety which occur naturally or are inserted by genetic engineering (see below). The means of linking moieties may also use thioether linkages between heterobifunctional crosslinking reagents or specific low pH cleavable crosslinkers or specific protease cleavable linkers or other cleavable or noncleavable chemical linkages. The means of linking moieties of the fusion proteins may also comprise a peptidyl bond formed between moieties which are separately synthesized by standard peptide synthesis chemistry or recombinant means.

In the case of chemical conjugation between the polypeptide and a non-proteinaceous functional moiety, a covalent bond between the two is preferred. Examples of active sites on the polypeptide or on the functional moiety for covalent bonds include sulfhydryl-reactive groups (e.g., methanethiosulfonyl groups, dithiopyridyl groups, other reactive disulfides, and cystine), alkylating agents (e.g., α-halo ketones, α-diazo ketones), and acylating agents (e.g., activated esters such as 2,4-dinitrophenyl esters and pentafluorophenyl esters, and certain anhydrides). Other suitable active sites are known to those of skill in the art.

However, covalent bonding of the polypeptide and the functional moiety of this invention is not required for the compounds of the present invention. Non-covalent bonding can take place via suitable electrostatic interactions with, for example, ammonium ion and carboxylic acid groups present in the polypeptide or in the functional moiety.

In one embodiment, the polypeptide and the functional moiety are linked in a non-continuous manner. For example, a linking group between the polypeptide and the functional moiety may comprise of two parts, which are selected to be complimentary binding groups, for example, two complimentary oligonucleotides or an avidin-biotin pair. Other complementary binding groups will be apparent to those of skill upon review of this disclosure.

In addition to the chemical modifications made to the polypeptides and the functional moieties prior to linking, chemical modifications of the polypeptides and the fusion proteins themselves are envisioned. Such modifications include but are not limited to, derivitization with polyethylene glycol (PEG) to extend time of residence in the circulatory system and reduce immunogenicity, according to well known methods (see for example, Lisi, et al., *Applied Biochem.* 4:19 (1982); Beauchamp, et al., *Anal. Biochem.* 131:25 (1982); and Goodson, et al, *Bio/Technology* 8:343 (1990)).

2. Recombinant Synthesis of Polypeptides and Fusion Proteins

In another embodiment, the polypeptides and the fusion proteins of this invention are synthesized recombinantly. Recombinant techniques are well known to those of skill and are described, in brief, below. The nucleic acids which encode the polypeptides and the functional moieties, whether RNA, cDNA, genomic DNA, or a hybrid of the various combinations, are isolated from biological sources or synthesized in vitro.

The nucleic acids which encode the polypeptides and functional moieties of this invention can be found in either genomic or cDNA libraries. For example, nucleic acids which encode the polypeptides of this invention can be found in human genomic libraries, nucleic acids which encode cell targeting antibodies can be found in spleen cells from immunized animals, and nucleic acids which encode for toxins can be found in the source bacteria, e.g., *Pseudomonas aeruginosa* and *Corynebacterium diphtheriae*. Methods for generating these libraries from source organisms, e.g., animals or bacteria, are known to those of skill and can be found in many practice guides, including Berger & Kimmel, *Guide to Molecular Cloning Techniques, Methods in Enzymology Vol.* 152, Academic Press, Inc., San Diego, CA (Berger); Sambrook et al. *Molecular Cloning—A Laboratory Manual* (2nd Ed.) Vol. 1–3, Cold Springs Harbor Publishing (1989) (Sambrook); and *Current Protocols in Molecular Biology*, Ausubel et al.(eds.), Current Protocols, a joint venture between Greene Publishing Associates, Inc. and John Wiley & Sons, Inc., (1997 Supplement) (Ausubel). Product information from manufacturers of biological reagents and experimental equipment also provide information useful in established biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to those of skill.

After the libraries have been created, the colonies must be probed to identify those colonies that contain the DNA of interest. Nucleic acid probes are nucleotide sequences that specifically hybridize under stringent conditions to the desired nucleic acid. Because the amino acid as well as the nucleotide sequence of Saposin B is known, generating probes to isolate clones with desired DNA would be considered routine and is not a critical aspect of this invention. In a preferred embodiment, the probes are chemically synthesized with a DNA synthesizer, amplified using the primers as shown in SEQ ID NOS:3 and 4, and expanded by cloning into a bacterial vector. The probes are then labeled by techniques well known in the art and the library is screened. Screening techniques with labeled nucleic acid probes is also well known in the art.

Stringent conditions for hybridization is dependent on the nucleic acid to be hybridized. An extensive guide to the hybridization of nucleic acids is found in Tijssen, *Laboratory Techniques in Biochemistry and Molecular Biology—Hybridization with Nucleic Acid Probes Parts I and Ii*, Elsevier, N.Y., (1993). Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Highly stringent conditions are selected to be equal to the Tm point for a particular probe. Sometimes the term "Td" is used to define the temperature at which at least half of the probe dissociates from a perfectly matched target nucleic acid. In any case, a variety of estimation techniques for estimating the Tm or Td are available, and generally described in Tijssen, id. Typically, G-C base pairs in a duplex are estimated to contribute about 3° C. to the Tm, while A-T base pairs are estimated to contribute about 2° C., up to a theoretical maximum of about 80–100° C. However, more sophisticated models of TM and Td are available and appropriate in which G-C stacking interactions, solvent effects, the desired assay temperature and the like are taken into account. In one example, PCR primers are designed to have a dissociation temperature (Td) of approximately 60° C., using the formula: Td' $(((((3 \times \#GC) + (2 \times \#AT)) \times 37) - 562)/\#bp) - 5$; where #GC, #AT, and #bp are the number of guanine-cytosine base pairs, the number of adenine-thymine base pairs, and the number of total base pairs, respectively, involved in the annealing of the primer to the template DNA.

In general, a signal to noise ratio of 2x (or higher) than that observed for an unrelated probe in the particular hybridization assay indicates detection of a specific hybridization. For highly specific hybridization strategies such as allele-specific hybridization, an allele-specific probe is usually hybridized to a marker nucleic acid (e.g., a genomic nucleic acid, or the like) comprising a polymorphic nucleotide under highly stringent conditions.

In addition to using nucleic acid probes for isolating the class of proteins claimed herein, it is possible to use antibodies to probe expression libraries for novel forms of active polypeptides. This is a well known technology (See Young & Davis, *Proc. Nat'l Acad. Sci. USA* 80:1194 (1982)). In general, a cDNA expression library may be prepared from commercially available kits or using readily available components. Phage vectors are preferred, but a variety of other vectors are available for the expression of protein. Such vectors include but are not limited to yeast, animal cells and Xenopus oocytes. One selects mRNA from a source that is enriched with the target protein and creates cDNA which is then ligated into a vector and transformed into the library host cells for immunoscreening. Screening involves binding and visualization of antibodies bound to specific proteins on library host cells or immobilized on a solid support such as nitrocellulose or nylon membranes. Positive clones are selected for purification to homogeneity and the isolated cDNA then prepared for expression in the desired recombinant cells. A general review of this technology can be found in *Methods of Cell Biology*, Vol. 37 entitled Antibodies in Cell Biology, Assai (ed.) 1993.

In addition, one of skill will realize that in some instances, the nucleic acid encoding a functional moiety does not have to be generated from a nucleic acid library. For example, transformed bacteria comprising nucleic acid sequences which encode bacterial exotoxins are available, as are transformed bacteria and mammalian cell lines which comprise nucleic acids which encode monoclonal or single chain antibodies (see Chaudhary, infra).

After the libraries described above have been screened and colonies with the appropriate DNA selected, the DNA is cloned according to techniques described in Sambrook, Ausubel and other literature available to those in the molecular biology field. To clone the polypeptides of this invention, the cells of a library which contain the desired DNA are selected and expanded. The genomic DNA from the culture is isolated and the inserted DNA of choice is purified. Typically, as an initial step, the desired nucledtide sequence is cleaved from the genomic or episomal DNA by restriction enzymes. After electrophoresis to separate the DNA on the basis of size, the nucleotide of interest is excised from the gel and inserted into an expression vector. For expression of the peptides of this invention, any suitable cell may be used, including, but not limited to, bacteria, insect, plant and mammal.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, Innis and Ausubel, as well as U.S. Pat. No. 4,683,202; Arnheim & Levinson, *C&EN* 36–47 (Oct. 1, 1990); Kwoh, et al., *Proc. Nat'l Acad. Sci. USA* 86:1173 (1989); Guatelli, et al., *Proc. Nat'l Acad. Sci. USA* 87:1874 (1990); Lomell, et al., *J. Clin. Chem.* 35:1826 (1989); Landegren, et al., *Science* 241:1077–1080 (1988); Van Brunt, *Biotechnology* 8:291–294 (1990); Wu & Wallace, *Gene* 4:560 (1989); Barringer, et al., *Gene* 89:117 (1990); and Sooknanan & Malek, *Biotechnology* 13:563–564 (1995). Improved methods of cloning in vitro amplified nucleic acids are described in U.S. Pat. No. 5,426,039.

In a preferred embodiment, the nucleic acid sequences which encode the polypeptides of this invention are amplified with primers that correspond to SEQ ID NOS:3 through 5. These primers are specific for Saposin B (SEQ ID NOS:3 and 4) and proSaposin (SEQ ID NOS:5 and 6).

Oligonucleotides for use as probes and primers are typically synthesized chemically according to the solid phase phosphoramidite triester method described by Beaucage & Caruthers, *Tetrahedron Letts.* 22(20):1859–1862 (1981), e.g., using an automated synthesizer, e.g., as described in Needham-VanDevanter, et al., *Nucl Acids Res.* 12:6159–6168 (1984). Oligonucleotides can also be custom made and ordered from a variety of commercial sources known to persons of skill, for example, Promega (Madison, Wis.). Purification of oligonucleotides, where necessary, is typically performed by either native acrylamide gel electrophoresis or by anion-exchange HPLC as described in Pearson & Regnier, *J. Chrom.* 255:137–149 (1983). The sequence of the synthetic oligonucleotides can be verified using the chemical degradation method of Maxam & Gilbert, *Methods in Enzymology* 65:499–560 (1980).

In some embodiments of this invention, it may be desirable to change an amino acid within a polypeptide or to truncate the polypeptide before the naturally occurring carboxyl terminus. There are many ways of generating alterations in a given nucleic acid sequence to effect substitutions of amino acid or to insert a stop codon to truncate the polypeptide. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman & Smith, *Gene* 8:81–97 (1979); Roberts, et al., *Nature* 328:731–734 (1987); Sambrook; Innis, Ausubel, Berger, Needham VanDevanter and Mullis (all supra).

Another preferred genetic engineering modifications of the polypeptides or the fusion proteins of this invention include combination of the polypeptide and the functional moiety into a single chain multi-functional protein expressed from a single gene. (See, for example, PCT published application WO8809344). Accordingly, the fusion protein will then comprise a polypeptide beginning at one end with the polypeptide and ending with the functional moiety. The recombinant linking of the polypeptide and the functional moiety can take place at either end of either molecule. For example, the carboxyl terminus of the polypeptide can be linked to the amino terminal of the functional moiety, or vice versa. Similarly, if desired, the polypeptide can be inserted into the interior of the functional moiety amino acid sequence. However, one must realize that, unless the polypeptide is small, activity of the functional moiety may be lost.

Methods of producing recombinant fusion proteins are well known to those of skill in the art. Thus, for example, Chaudhary, et al., *Nature* 339:394 (1989); Batra, et al., *J. Biol. Chem.* 265:15198 (1990); Batra, et al., *Proc. Nat'l Acad. Sci. USA* 86:8545 (1989); Chaudhary, et al., *Proc. Nat'l Acad. Sci. USA* 87:1066 (1990), describe the preparation of various single chain fusion proteins.

In general, producing fusion proteins involves separately preparing the polypeptide nucleic acid sequence and DNA encoding the functional moiety to be used. The two sequences are combined in a plasmid or other vector to form a construct encoding the particular desired fusion protein. A simpler approach involves inserting the DNA encoding the particular polypeptide into a construct already encoding the desired functional moiety.

Thus, for example, DNA encoding a polypeptide-Pseudomonas exotoxin fusion protein is most easily prepared by inserting the DNA encoding the polypeptide into constructs already containing DNA encoding the desired exotoxin using techniques well known to those of skill in the art.

Mammalian cells have been used to express and secrete polypeptides and hybrid molecules such as antibody-cytokines (Hoogenboom, et al., *Biochem. Biophys. Acta* 1096:345 (1991); Hoogenboom, et al., *Mol. Immunol.* 28:1027 (1991)) and antibody-enzyme (Casadei, et al., *Proc. Nat'l Acad. Sci. USA* 87:2047 (1990); Williams, et al., *Gene* 43:319 (1986)). A drawback to using recombinant proteins is the potential immunogenicity of the foreign proteins. Immunogenicity of foreign proteins is typically due to incorrect glycosylation patterns present on recombinant proteins. Therefore, because the expressed proteins are glycosylated, eukaryotic cell lines are preferred over prokaryotic cells. In particular, human derived cell lines are particularly preferred in that these cells incorporate a sialic acid as the terminal glycoside.

Although human cells are desirable because of decreased immunogenicity, one of skill will realize that other cells can be used to express the peptides of this invention. For example, mammalian cell lines like CHO, COS, 3T3 and L cells can be used. Other eukaryotic cells that can be used include, but are not limited to insect cell lines and yeast cells, e.g., *Saccharomyces cerevisiae* and *Pichia pasteris*. In addition, if glycosylation is not critical, the peptides of this invention can be expressed in prokaryotic cells, for example, *E. coli*.

One of skill will recognize that modifications can be made to the polypeptides without diminishing their anti-angiogenic activity. Some modifications may be made to facilitate the cloning, expression, or incorporation of the anti-angiogenic moiety into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Other genetic engineering modifications of the protein moieties of the fusion proteins of this invention include deletions of functionally unnecessary domains to reduce the size of the protein or to modify other parameters which facilitate production or utility, such as sequence changes to affect the solubility (e.g., cysteine to serine) or glycosylation sites. One skilled in the art would appreciate that many additional well known chemical and genetic modifications of proteins may be advantageously applied to any protein which, like the present fusion protein, may be intended for parenteral administration.

3. Chemical Synthesis of the Peptides

The polypeptides of this invention are preferably synthetically prepared. Polypeptides of relatively short size are typically synthesized in solution or on a solid support in accordance with conventional techniques. See, e.g., Merrifield, *J. Am. Chem. Soc.* 85:2149 (1963). Various automatic synthesizers and sequencers are commercially available and can be used in accordance with known protocols. See, e.g., Stewart & Young, *SOLID PHASE PEPTIDE SYNTHESIS*, 2d. Ed., Pierce Chemical Co (1984). Solid phase synthesis in which the carboxyl terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany & Merrifield, *Solid-Phase Peptide Synthesis*; pp. 3–284 in *The Peptides: Analysis, Synthesis, Biology. Vol. 2: Special Methods in Peptide Synthesis, Part A*.,; Merrifield, et al., *J. Am. Chem. Soc.* 85: 2149–2156 (1963); and Stewart, et al., *Solid Phase Peptide Synthesis, 2nd Ed.* Pierce Chem. Co., Rockford, Ill. (1984).

After chemical synthesis or recombinant expression, the polypeptide(s) may possess a conformation substantially different than the native conformation of the polypeptides. In this case, it is helpful to denature and reduce the polypeptide and then cause the polypeptide to re-fold into the preferred conformation. Methods of reducing and denaturing polypeptides and inducing re-folding are well known to those of skill in the art (see, Debinski, et al. *J. Biol. Chem.* 268:14065 (1993); Kreitman & Pastan, *Bioconjug. Chem.* 4:581 (1993); and Buchner, et al., *Anal. Biochem.* 205:263 (1992)). Debinski, et al., for example, describe the denaturation and reduction of inclusion body polypeptides in guanidine-DTE. The polypeptide is then refolded in a redox buffer containing oxidized glutathione and L-arginine.

In addition to polypeptides consisting of a peptide backbone, peptidomimetics or polypeptide analogs are also provided. Polypeptide analogs are commonly used in the pharmaceutical industry as non-peptide drugs with properties analogous to those of the template polypeptide. These types of non-peptide compound are termed "peptide mimetics" or "peptidomimetics" (Fauchere, J., *Adv. Drug Res.* 15:29 (1986); Veber & Freidinger, *TINS* p.392 (1985); and Evans et al., *J. Med. Chem.* 30:1229 (1987)). Peptide mimetics that are structurally similar to the useful polypeptides of this invention may be used to produce an equivalent or enhanced anti-angiogenic effect.

Generally, peptidomimetics are structurally similar to a paradigm polypeptide, i.e., Saposin B or a polypeptide with anti-angiogenic activity, but have one or more peptide linkages optionally replaced by a linkage selected from the group consisting of: —$CH_2NH$—, —$CH_2S$—, —$CH_2$—$CH_2$—, —CH—CH— (cis and trans), —$COCH_2$—, —CH(OH)$CH_2$—, and —$CH_2SO$—, by methods known in the art and further described in the following references: Spatola, *Chemistry and Biochemistry of Amino Acids, Peptides, and Proteins*, B. Weinstein, (ed.), Marcel Dekker, New York, p. 267 (1983); Spatola, *Vega Data* 1(3), Peptide Backbone Modifications (general review) (March 1983); Morley, *Trends Pharm. Sci.* (1980) pp. 463–468 (general review); Hudson, et al., *Int'l J. Pept. Prot. Res.* 14:177–185 (1979) (—$CH_2NH$—, $CH_2CH_2$—); Spatola, et al., *Life Sci.* 38:1243–1249 (1986) (—$CH_2$—S); Hann, *J. Chem. Soc. Perkin Trans. I* 307–314 (1982) (—CH—CH—, cis and trans); Almquist, et al., *J. Med Chem.* 23:1392–1398 (1980) (—$COCH_2$—); Jennings-White, et al., *Tetrahedron Lett.* 23:2533 (1982) (—$COCH_2$—); Szelke, et al., EP 45665 (1982) (—CH(OH)$CH_2$—); Holladay, et al., *Tetrahedron Lett.* 24:4401–4404 (1983) (—C(OH)$CH_2$—); and Hruby, *Life Sci.* 31:189–199 (1982) (—$CH_2$—S—). Thus, in the instant invention, an anti-angiogenic peptidomimetic would be structurally similar to the polypeptides of this invention, i.e., comprises $DX_1CX_2D$.

Peptide mimetics may have significant advantages over polypeptide embodiments of this invention, including, for example: more economical production, greater chemical stability, enhanced pharmacological properties (half-life, absorption, potency, efficacy, etc.), altered specificity (e.g., a broad-spectrum of biological activities), reduced antigenicity, and others.

Chemical conjugation of peptidomimetics to make fusion proteins usually involves covalent attachment to one or more binding sites on the functional moieties, directly or through a spacer (e.g., an amide group), to non-interfering position (s) on the peptidomimetic that are predicted by quantitative structure-activity data and/or molecular modeling. Such non-interfering positions generally are positions that do not form direct contacts with the surface macromolecules(s) (e.g., Saposin B receptors on KS cells) to which the peptidomimetic binds to produce the anti-angiogenic effect. In addition, derivitization (e.g., labeling) and conjugation of peptidomimetics should not substantially interfere with the desired anti-angiogenic activity of the peptidomimetic.

In addition to the peptidomimetics, synthetic polypeptides can comprise systematic substitution of one or more amino acids with a D-amino acid of the same type (e.g., D-lysine in place of L-lysine). These substitutions may be used to generate more stable polypeptides. Also, constrained polypeptides comprising a consensus sequence or a substantially identical consensus sequence variation may be generated by methods known in the art (Rizo & Gierasch, *Ann. Rev. Biochem.* 61:387 (1992)); for example, by adding internal cysteine residues capable of forming intramolecular disulfide bridges which cyclize the peptide.

In addition to modifications to the peptide backbone, synthetic or non-naturally occurring amino acids can also be used to substitute for the amino acids present in the polypeptide or in the functional moiety of fusion proteins. Synthetic or non-naturally occurring amino acids refer to amino acids which do not naturally occur in vivo but which, nevertheless, can be incorporated into the peptide structures described herein. Preferred synthetic amino acids are the D-α-amino acids of naturally occurring L-α-amino acid, mentioned above, as well as non-naturally occurring D- and L-α-amino acids represented by the formula $H_2NCHR^5COOH$ where R' is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5) -alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —C(O)$R^2$ where $R^2$ is selected from the group consisting of hydrogen, hydroxy, lower alkyl, lower alkoxy, and —$NR^3R^4$ where $R^3$ and $R^4$ are independently selected from the group consisting of hydrogen and lower alkyl, (g) —$S(O)_nR^6$ where n is an integer from 1 to 2 and $R^6$ is lower alkyl and with the proviso that $R^5$ does not define a side chain of a naturally occurring amino acid.

Other preferred synthetic amino acids include amino acids wherein the amino group is separated from the carboxyl group by more than one carbon atom such as β-alanine, γ-aminobutyric acid, and the like.

Particularly preferred synthetic amino acids include, by way of example, the D-amino acids of naturally occurring L-amino acids, L-1-naphthyl-alanine, L-2-naphthylalanine, L-cyclohexylalanine, L-2-amino isobutyric acid, the sulfoxide and sulfone derivatives of methionine (i e., HOOC—$(H_2NCH)CH_2CH_2$—$S(O)_nR^6$) where n and $R^6$ are as defined above as well as the lower alkoxy derivative of methionine (i.e., HOOC—$(H_2NCH)CH_2CH_2$—$OR^6$ where $R^6$ is as defined above).

B. Characterization of the Peptides and Fusion Proteins

It is necessary, especially when synthesizing fusion proteins, to determine whether the polypeptides or fusion proteins have desired characteristics and thus will be anti-angiogenic. Characterization can be done either by the structural or chemical properties of the polypeptides or fusion proteins, or by the functional properties of the polypeptides or fusion proteins.

1. Physical and Chemical Characterization of the Peptides

Polypeptides and fusion proteins may be detected or quantified by a variety of methods. Preferred methods involve the use of immunological assays utilizing specific antibodies.

a. Antibodies

Methods of producing polyclonal and monoclonal antibodies are known to those of skill in the art. See, e.g., Coligan, *Current Protocols in Immunology*, Wiley/Greene, NY (1991); Stites, et al. (eds.) *BASIC AND CLINICAL IMMUNOLOGY* (7th Ed.) Lange Medical Publications, Los Altos, Calif., and references cited therein ("Stites"); Goding, *Monoclonal Antibodies: Principles and Practice* (2d Ed.) Academic Press, New York, N.Y. (1986); Kohler & Milstein, *Nature* 256:495 (1975); and Harlow and Lane. Such techniques include antibody preparation by selection of antibodies from libraries of recombinant antibodies in phage or similar vectors. See, Huse, et al., *Science* 246:1275 (1989) ("Huse"); and Ward, et al., *Nature* 341:544 (1989).

To produce polyclonal antibodies, in brief, an immunogen, e.g., a polypeptide of this invention, is mixed with an adjuvant, and animals are immunized. The animal's immune response to the immunogen preparation is monitored by taking test bleeds and determining the titer of reactivity to the immunogen. When appropriately high titers of antibody to the immunogen are obtained, blood is collected from the animal and antisera are prepared. Further fractionation of the antisera to enrich for antibodies reactive to the protein may be done if desired. (See Harlow and Lane, supra).

Antibodies can only be raised against macromolecules. Therefore, it is likely that an immune response will not be mounted against the smaller polypeptides of this invention. To generate antibodies against such small molecules, it is first necessary to associate them with larger macromolecules which will be recognized by the animal's immune system. Briefly, the polypeptide is conjugated to carrier proteins according to the methods described in the preceding sections. Typical carrier proteins are bovine serum albumin, keyhole limpet cyanin and ovalbumin. The animals are immunized with the carrier proteins associated with the polypeptide and bleeds collected as above. Only the polypeptide (without the carrier protein) is used to screen the test bleeds for reactivity to the polypeptide.

Large amounts of monoclonal antibodies may be obtained by various techniques familiar to those skilled in the art. Briefly, spleen cells from an animal immunized with a desired protein (either a fusion protein or a polypeptide of this invention, or a polypeptide associated with a carrier protein) are immortalized, commonly by fusion with a myeloma cell (See, Kohler & Milstein, *Eur. J. Immunol.* 6:511 (1976)). Alternative methods of immortalization include transformation with Epstein Barr Virus, oncogenes, retroviruses, or other methods well known in the art. Colonies arising from single immortalized cells are screened for production of antibodies of the desired specificity and affinity for the polypeptides or fusion proteins of this invention. The yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined in Huse.

2. Immunological Binding Assays.

The concentration of the polypeptides and fusion proteins can be measured by a variety of immunoassay methods. For a review of immunological and immunoassay procedures in general, see Stites. Moreover, the immunoassays of the present invention can be performed in any of several configurations, which are reviewed extensively in *Enzyme Immunoassay*, E. T. Maggio, ed., CRC Press, Boca Raton, Fla. (1980); Tijssen; and Harlow and Lane.

In a preferred embodiment, the polypeptides and fusion proteins of this invention are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology Vol. 37: Antibodies in Cell Biology, Asai, ed. Academic Press, Inc. New York (1993); and Stites. Immunological binding assays (or immunoassays) typically utilize a "capture agent" to specifically bind to and often immobilize the analyte (in this case polypeptides, fusion proteins and the receptors). The capture agent is a moiety that specifically binds to the analyte. In a preferred embodiment, the capture agent is an antibody that specifically binds to the polypeptides, fusion proteins and receptors of this invention. The antibody may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, for example, the labeling agent may be a labeled polypeptide or a labeled anti-polypeptide antibody. Alternatively, the labeling agent may be a third moiety, such as another antibody, that specifically binds to the antibody/polypeptide complex.

In a preferred embodiment, the labeling agent is a second polypeptide or receptor antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401–1406 (1973), and Akerstrom, et al., *J. Immunol.* 135:2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 4° C. to 40° C.

In addition to the EIA based formats described above, western blot (immunoblot) analysis can be used to detect and quantify the presence of antifreeze protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind THP. The anti-THP antibodies specifically bind to THP on the solid support. These antibodies may be directly labeled or alternatively may be subsequently detected using labeled antibodies (e.g., labeled sheep anti-mouse antibodies) that specifically bind to the anti-antifreeze protein.

Other assay formats include liposome immunoassays (LIA), which use liposomes designed to bind specific molecules (e.g., antibodies) and release encapsulated reagents or markers. The released chemicals are then detected according to standard techniques (see, Monroe, et al., *Amer. Clin. Prod Rev.* 5:34 (1986)).

3. Functional Characterization of the Peptides

Functional characterization of the polypeptides of this invention takes advantage of their anti-angiogenic antiproliferative properties. In other words, the anti-angiogenic and/or anti-proliferative potential of the polypeptides is measured. In a preferred embodiment, the anti-proliferative activity of the polypeptides of this invention are measured in cells of endothelial origin, e.g., HUVEC and murine endothelial cells, and Kaposi's Sarcoma cell lines, e.g., KS, Y-1, KS-SLK and KS 6-3. However, one of skill will realize that any cell line that responds to anti-angiogenic or anti-tumoral factors can be used to functionally characterize the polypeptides of this invention.

Typically, in an anti-proliferation assay, the suppression of growth in the presence of the compound to be tested is measured. For example, the above cells are incubated with the polypeptides of this invention for a suitable time and the decrease in the growth rate relative to a negative control, i.e., cells of the same cell line which have been incubated in media alone, is measured. Growth of the cell culture can be measured by any method acceptable to one of skill, including but not limited to, 3H-thymidine uptake, cell counting and tetrazolium dye uptake.

Anti-angiogenic assays measure the functional inhibition of endothelial cells by a compound in the presence of a chemotactic factor known to activate endothelial cells, e.g., VEGF and bFGF. In a typical conformation, endothelial cells along with the compound to be tested are placed in the upper chamber of a two-chamber well, e.g., Boyden chambers or transwell plates. Media with a chemotactic factor is placed in the lower chamber. Dividing the two chambers is a membrane that is permeable to the chemotactic factor but not to the endothelial cells. The membrane can be covered with a basement membrane, either natural or artificial, e.g., Matrigel. Alternatively, the membrane can be coated with fibronectin or another protein capable of forming a gel susceptible to protease degradation. The plates with the endothelial cells are incubated for a sufficient time to allow the cells to traverse the membrane. To determine the anti-angiogenic activity of the compound, the number of cells that traversed the membrane in the presence of the compound is compared to the number of cells that traversed the membrane without the compound. If the number of cells in the lower chamber (or on the aspect of the membrane in contact with the chemotactic factor) is less than the number of cells in the control chamber, the compound had anti-angiogenic potential.

In addition to the relatively simple assay described above, the polypeptides and fusion proteins of this invention may be functionally characterized in a multi-system angiogenic assay. For example, the most commonly used multi-system assay utilizes the allantoic membrane of the developing chick embryo. A window is cut into the egg shell, exposing the allantoic membrane. The polypeptide to be tested is added to the membrane and the egg is incubated long enough for the anti-angiogenic effect of the compound to be visible, e.g., fewer blood vessels in the allantoic membrane compared to a negative control.

In another in vivo assay, tumor cell lines are implanted into nude mice. The mice are then treated with the polypeptides and fusion proteins of this invention. After a suitable time, the mice are observed for signs of tumor regression. If the tumor has regressed or decreased in size, the compound being tested has anti-angiogenic or anti-tumor properties. See, Arora, et al., *Cancer Research* 59:183 (1999).

The fusion proteins of this invention can be further characterized by the activity of the functional moiety. One of skill will realize that these proteins can be characterized by the same assays used to characterize the functional moiety alone. For example, assays to measure the cytotoxic effect of bacterial toxins can be used to measure the cytotoxic activity of fusion proteins comprising the polypeptides of this invention conjugated to Pseudomonas exotoxin or Diphtheria toxin. One example of a cytotoxic assay, not intended to be limiting, can be found in Galloway, *J. Immunol. Methods* 140:37 (1991).

C Receptors of this Invention

Another embodiment of this invention comprises the isolated receptors that bind to the polypeptides of this invention. The isolated receptors can be used to screen for other anti-angiogenic or anti-tumor drugs. In addition, the isolated receptors may themselves be used as an angiogenic drug. For example, if angiogenesis is desired, e.g., wound healing, the isolated receptors of this invention can be administered to a mammal, compete for Saposin B binding (or other anti-angiogenic compounds) with the receptors present on the endothelial cells, and promote the migration of endothelial cells through the basement membrane of existing blood vessels.

Isolation of cell surface receptors is known to those of skill in the art. Briefly, cells known to comprise the receptors of this invention are solubilized with a lipophilic agent, typically an ionic detergent. The cell lysate is then affinity purified by passing it through a column packed with a resin to which the polypeptides of this invention have been conjugated. The bound receptors are eluted from the column, typically in high salt or if necessary, an ionic detergent. The receptors can be further purified to homogeneity by further column purification or by preparative electrophoresis.

It is anticipated that the numbers of receptors present on cells is very small and the techniques outlined above will not generate sufficient receptors to use in drug screening assays or as angiogenesis promoting pharmaceuticals. Therefore, it may be necessary to recombinantly express the receptors of this invention. Again, genomic or cDNA libraries can be probed either with nucleic acids or with antibodies or polypeptides that specifically bind to the receptors of this invention. To make degenerate nucleic acid probes, the naturally occurring receptors described above can be sequenced according to techniques well known in the art and described herein. Using the appropriate preferred codons, nucleic acid probes are synthesized and labeled. Because it is likely that nucleotide mismatches will occur (because of codon degeneracy), the hybridization of the probe to the membrane to which the library has been transferred, should not be as stringent as described above. Colonies which contain DNA that hybridized to the degenerate probes are isolated and expanded as described above.

To screen an expression library, either antibodies raised against the purified naturally-occurring receptor or the polypeptides of this invention can be used. The general techniques of screening the expression library are as described herein.

The receptors of this invention can be characterized using the assays described above. However, the desired results will be the opposite of the results obtained with the polypeptides of this invention, i. e., increase angiogenesis or proliferation in the presence of Saposin B or the polypeptides of this invention is desired.

D. Saposin B Antibodies

In addition to characterizing the peptides of this invention, antibodies directed against Saposin B can be used as a therapeutic treatment to encourage angiogenesis.

Saposin B is expressed by cells as an element in the homeostasis of cell growth. Thus, in situations where angiogenesis is desired but blocked by the presence of Saposin B, compositions which inhibit the action of Saposin B will block this protein's activity. The compositions include, but are not limited to, Saposin B receptors (see above) and neutralizing antibodies directed against Saposin B.

Thus, the present invention provides antibodies targeted to Saposin B and/or the peptides of this invention. These antibodies are selectively reactive under immunological conditions to determinants of Saposin B exposed on the protein surface and accessible to the antibody from the extracellular milieu.

The term "selectively reactive" includes reference to the preferential association of an antibody, in whole or part, with a Saposin B determinant or peptide and not to proteins, cells or tissues lacking that target determinant. It is, of course, recognized that a certain degree of non-specific interaction may occur between a molecule and a non-target cell or tissue. Nevertheless, specific binding, may be distinguished as mediated through specific recognition of the target Saposin B molecule. Typically specific binding results in a much stronger association between the delivered antibody and Saposin B than between the bound molecule and proteins or cells lacking Saposin B. Specific binding typically results in greater than 2 fold, preferably greater than 5 fold, more preferably greater than 10 fold and most preferably greater than 100 fold increase in amount of bound ligand (per unit time) to Saposin B or a cell or tissue bearing Saposin B as compared to a protein, cell or tissue lacking a Saposin B determinant. The immunoassay formats listed above are appropriate for selecting antibodies specifically immunoreactive with a particular protein.

In some embodiments of the present invention, the anti-Saposin B antibody is an antibody binding fragment such as an scFv or dsFv antibody. Fv fragments are typically about 25 kDa and contain a complete antigen-binding site. The $V_H$ and $V_L$ chains of the Fv fragments are held together by noncovalent interactions. These chains tend to dissociate upon dilution, so methods have been developed to crosslink the chains through glutaraldehyde, intermolecular disulfides, or a peptide linker. In some preferred embodiments, the Fv antibody binding fragment has a variable heavy chain from an antibody directed against Saposin B or a conservatively modified variant thereof, and/or a variable light chain from an antibody directed against Saposin B or conservatively modified variant thereof. Such conservative variants employed in dsFv fragments will retain cysteine residues used for disulfide linkages between the chains. Conservatively modified variants of the anti-Saposin B $V_H$ and $V_L$ have at least 80% sequence similarity, preferably at least 85% sequence similarity, more preferably at least 90% sequence similarity, and most preferably at least 95% sequence similarity at the amino acid level to a nucleic acid sequence of the $V_H$ and $V_L$ of a monoclonal antibody directed against Saposin B.

Methods of making Fv antibodies have been described. See, Huse, et al., *Science* 246:1275–1281 (1989); and Ward, et al., *Nature* 341:544–546 (1989); and Vaughan, et al., *Nature Biotechnology* 14:309–314 (1996). In general, suitable monoclonal or polyclonal antibodies will usually bind with an affinity constant of at least $10^{-6}$ M, preferably at least $10^{-8}$ M, preferably at preferably at least $10^{-9}$M, more preferably at least $10^{-10}$ M, most preferably at least $10^{-11}$ M.

The variable heavy and light chains ($V_H$ and $V_L$) of disulfide stabilized Fv fragments are covalently linked via a disulfide linkage between cysteine residues present in each of the two chains. The pair of amino acids to be selected are, in order of decreasing preference:

$V_H44$-$V_L100$
$V_H105$-$V_L43$,
$V_H105$-$V_L42$,
$V_H106$-$V_L43$,
$V_H104$-$V_L43$,
$V_H4$-$V_L99$,
$V_H5$-$V_L98$,
$V_H6$-$V_L98$,
$V_H103$-$V_L43$,
$V_H103$-$V_L44$,
$V_H103$-$V_L45$.

Most preferably, substitutions of cysteine are made at the positions:

$V_H44$-$V_L100$; or
$V_H105$-$V_L43$.

The notation $V_H44$-$V_L100$, for example, refers to a polypeptide with a $V_H$ having a cysteine at position 44 and a cysteine in $V_L$ at position 100; the positions being in accordance with the numbering given in "Sequences of Proteins of Immunological Interest," E. Kabat, et al., U.S. Government Printing Office, NIH Publication No. 91-3242 (1991); which is incorporated herein by reference ("Kabat and Wu"). DsFv fragments comprise at least one disulfide linkage but may comprise 2, 3, 4, 5 or more linkages as desired.

While the two $V_H$ and $V_L$ chains of some antibody embodiments can be directly joined together, one of skill will appreciate the molecules may be separated by a peptide linker consisting of one or more amino acids. Generally the peptide linker will have no specific biological activity other than to join the proteins or to preserve some minimum distance or other spatial relationship between them. However, the constituent amino acids of the peptide linker may be selected to influence some property of the molecule such as the folding, net charge, or hydrophobicity. Single chain Fv (scfv) antibodies optionally include a peptide linker of no more than 50 amino acids, generally no more than 40 amino acids, preferably no more than 30 amino acids, and more preferably no more than 20 amino acids in length.

II. PHARMACEUTICAL COMPOSITIONS OF THIS INVENTION

In one embodiment of this invention, the polypeptides of this invention are formulated into pharmaceutical compositions. In addition to the polypeptides of this invention, the pharmaceutical compositions of this invention comprise pharmaceutically acceptable carriers, including excipients. Throughout this section, the term polypeptide will be used to indicate the polypeptides, fusion proteins and receptors of this invention.

A. Purification of the Polypeptides and Fusion Proteins

It may be necessary to purify the polypeptides of this invention prior to formulation into a pharmaceutical composition of this invention. Protein purification techniques are well known in the art and can be found in many practice guides, including "Basic Protein and Peptide Protocols," *Methods in Molec. Biol. Vol.* 32, Walker, ed., Humana Press (1994).

After the polypeptides have been chemically synthesized by, for example, the peptide synthesis techniques described above, it may be necessary to remove the excess amino acids from the reaction mixture containing the polypeptides. Purification techniques suitable for removing amino acids are well known in the art. For example, the polypeptides may be purified using known chromatographic procedures such as reverse phase HPLC, gel permeation, ion exchange, size exclusion, affinity, partition, or countercurrent distribution (see, generally, R. Scopes, *Polypeptide Purification*, Springer-Verlag, N.Y. (1982), Deutscher, *Methods in Enzymology Vol.* 182: Guide to Polypeptide Purification., Academic Press, Inc. N.Y. (1990)). Once purified, partially or to homogeneity as desired, the polypeptides may then be used (e.g., as immunogens for antibody production, as anti-angiogenic moieties in fusion proteins, or as active compounds in pharmaceutical compositions).

B. Pharmaceutically Acceptable Carriers

Suitable formulations for use in the present invention are found in *Remington's Pharmaceutical Sciences* (Mack Publishing Company, Philadelphia, Pa., 17th ed. (1985)). Moreover, for a brief review of methods for drug delivery, see, Langer, *Science* 249:1527–1533 (1990). The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the polypeptides of this invention can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the polypeptides can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal and sublingual administration, the compositions may take the form of tablets or lozenges formulated in conventional manner.

For administration by instillation or inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in vaginal or rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for the polypeptides and fusion proteins of this invention may be employed. Liposomes and emulsions are well known examples of delivery vehicles or carriers for drugs. For transdermal delivery, certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic polypeptide. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount administered to the patient will vary depending upon severity of the undesired angiogenesis, the activity of the specific polypeptide being administered, the overall health of the patient and the manner of administration. The pharmaceutical compositions of this invention are administered to a patient already suffering undesirable angiogenesis and therefore, the composition is administered in an amount sufficient to ameliorate undesirable angiogenesis and its complications. An amount adequate to accomplish this is defined as "therapeutically effective dose." Generally, the dose for systemic use, e.g.,intravenous, intrathecal, and intraarterial, will be in the range of about 0.1 mg/kg to about 50 mg/kg per day, preferably about 5 mg/kg to about 20 kg/mg per day, for a 70 kg patient. One of skill will recognize upon review of this disclosure that the dose will also depend on the route of administration. For example, for local administration, e.g., topical, intravaginal, intrarectal, subcutaneous, and intraocular, the dose will be in the range of about 0.1 mg/cm$^2$ to about 2.5 mg/cm$^2$ per dose, preferably about 1 mg/cm$^2$ per dose.

III. EXAMPLES

Example 1

Activity of Recombinant Saposin B and Other Prosaposin Chains

In order to determine whether recombinant Saposin B has anti-angiogenic activity, the coding region of each of the Prosaposin chains was amplified from fibroblast cell lines and cloned into both bacterial (pGEX-KG) and eukaryotic (pcDNA 3.1His A) expression vectors.

A T1 fibroblast cell line (ATCC, Rockville, Md.) was grown in DMEM media containing 10% FBS. Total RNA was extracted from 4×106 cells by RNAzol reagent (Tel-Test, Friendswood, Tex.). About 5 μg of total RNA was used to synthesize cDNA (Life technologies, Gaithersburg, Md.) using either oligo dT or random primers. To amplify, Saposin B cDNA, two primers were synthesized to correspond to the 5' and 3' ends of the coding region (ATT CGA ATT CAA GGG GAC GTT TGC CAG GAC TGC (SEQ ID NO:3) and TTC TGT GAT GAG GTG AAA TAG CTC GAG CTC GAG (SEQ ID NO:4)). The primers were designed so that an Eco RI restriction site was located at the 5' end and a Xho I restriction site was located at the 3' end. Prosaposin, Saposin A, C and D were amplified from the same cDNA using primers that added aXbal restriction site at the 5' end and a Xhol restriction site at the 3' end of the amplified DNA. The primers used in the PCR amplification were: Prosaposin-CTA GAT CTA GAA ATG TAC GCC CTC TTC CTC CTG GCC (SEQ ID NO:5) and CTC GAG CTC GAG CTA GTT CCA CAC ATG GCG TTT GCA (SEQ ID NO:6); Saposin A-CTA GAT CTA GAA TCC CTT CCC TGC GAC ATA TCC (SEQ ID NO:7) and CTC GAG CTC GAG TCA CTT CTG GAG AGA CTC GCA GAG (SEQ ID NO:8); Saposin C-CTA GAT CTA GAA TCT GAT GTT TAC TGT GAG GTG (SEQ ID NO:9) and CTC GAG CTC GAG TCA TGC CAG AGC AGA GGT GCA GCA (SEQ ID NO:10); and Saposin D-CTA GAT CTA GAA GAC GGT GGC TTC TGC GAA GTG (SEQ ID NO:11) and CTC GAG CTC GAG TCA CTT ATG GGC CGA GGG GCA GGC (SEQ ID NO:12). The amplification reactions included incubation at 94° C. for 1 min to denature double stranded DNA, 55° C. for 2.5 min to anneal primers and 72° C. for 3 min to polymerase double stranded DNA. The reaction was repeated for 30 cycles. A final polymerization step was done at 72° C. for 10 min.

The PCR products were digested with the respective restriction enzymes and the restriction products were inserted into the pGEX-KG vector for bacterial expression. pGEX-KG vector comprises a glutathione S transferase (GST)-tag at the 3' end of the insertion site so that a GST-fusion protein is expressed. The GST-tag is used to aid in purification of the recombinant protein. After elution from a glutathione-Sepharose 4B column, the GST-tagged proteins were incubated with thrombin (4 μg/ml) for 4 hr at room temperature (22–25° C.) in 50 mM Tris, pH 8.3, 3 mM CaCl2, 150 mM NaCl to cleave GST from the fusion protein. Free GST was removed from the preparation by passing the digested fusion protein through the glutathione-Sepharose 4B column.

By SDS-PAGE, the bacterial product was smaller than the eukaryotic protein. Because prokaryotically expressed proteins are not glycosylated, the difference in molecular weights probably represents the presence of carbohydrate in the eukaryotic protein. Recombinant proteins were then tested in KS, endothelial and control cell lines. Activity was found only in KS cell lines and endothelial cells.

Recombinant Saposin C had no activity against KS cell lines and endothelial cells even at the highest concentration tested (50 μg/mL). Similarly Saposin A and D had no activity (data not shown). Naturally occurring full-length Prosaposih was also tested with, again, no activity. These findings demonstrate that only Saposin B exhibits anti-angiogenic activity. Similar results with anti-angiogenic proteins have previously been reported. For example, angiostatin is a cryptic peptide of prothrombin and endostatin is a carboxy peptide of collagen XVIII. Both angiostatin and endostatin have been reported to possess anti-angiogenic activity while their precursor proteins do not.

Example 2

Saposin B Inhibist Endothelial Cell Migration

Angiogenesis is mediated by complex biochemical processes including degradation of the basement membrane under existing blood vessel endothelial cells, followed by proliferation and migration of endothelial cells, followed by formation of capillary loops, and recruitment of vascular smooth muscle cells to encase the newly formed vessels and provide stability. KS and endothelial cell migration in the presence of Saposin B was studied in transwell culture plates with 8 μm pore membranes (Costar, Cambridge, Mass.).

Briefly, wells were coated with fibronectin (25 μg/mL) overnight, and endothelial cells or KS cells were plated in the upper chamber with 100 μL of DMEM/0.4% FCS. 500 μL of DMEM/0.4% FCS was added to the lower chamber and incubated at 37° C. for one hour. The test polypeptides, at various concentrations, were added to the upper chamber, and chemotactic agents (VEGF or bFGF at 20 ng/mL) were added to the lower cell-culture chambers. The plates were incubated for 5 hr at 37° C. and the cells crossing the fibronectin-coated membrane were counted after wiping the cells off the membrane in the upper chamber with a cotton swab.

The cells that traversed the membrane were fixed with Diff-Quik stain according to the manufacturer's instruction (Dade Diagnostics Inc., Aguada, PR). The cells were counted under a microscope at 320× in four randomly selected fields. The experiments were done in duplicate and repeated at least three times.

Recombinant Saposin B was found to be highly active with compete inhibition of cell migration. Thus, Saposin B is a strong inhibitor of endothelial and KS cell migration. For comparison, paclitaxel did not completely inhibit endothelial cell nigration.

Example 3

Saposin B Inhibits Angiogenesis in CAM Assays

In order to test anti-angiogenic activity, chicken allantoic membrane (CAM) assays were performed with recombinant Saposin B. Ten day old fertilized chicken eggs were prepared for assay by creating a window in the egg shell, and placing filter paper discs saturated with VEGF or bFGF as positive controls, test compounds, or carrier buffer (negative controls) on the allantoic membrane. The membranes were harvested after 48 hours and analyzed using an Olympus stereomicroscope. The number of branching blood vessels that infiltrated under the discs were counted and photographed. Eight CAMs were studied for test group, and the experiments were repeated at least twice.

Figure 3:
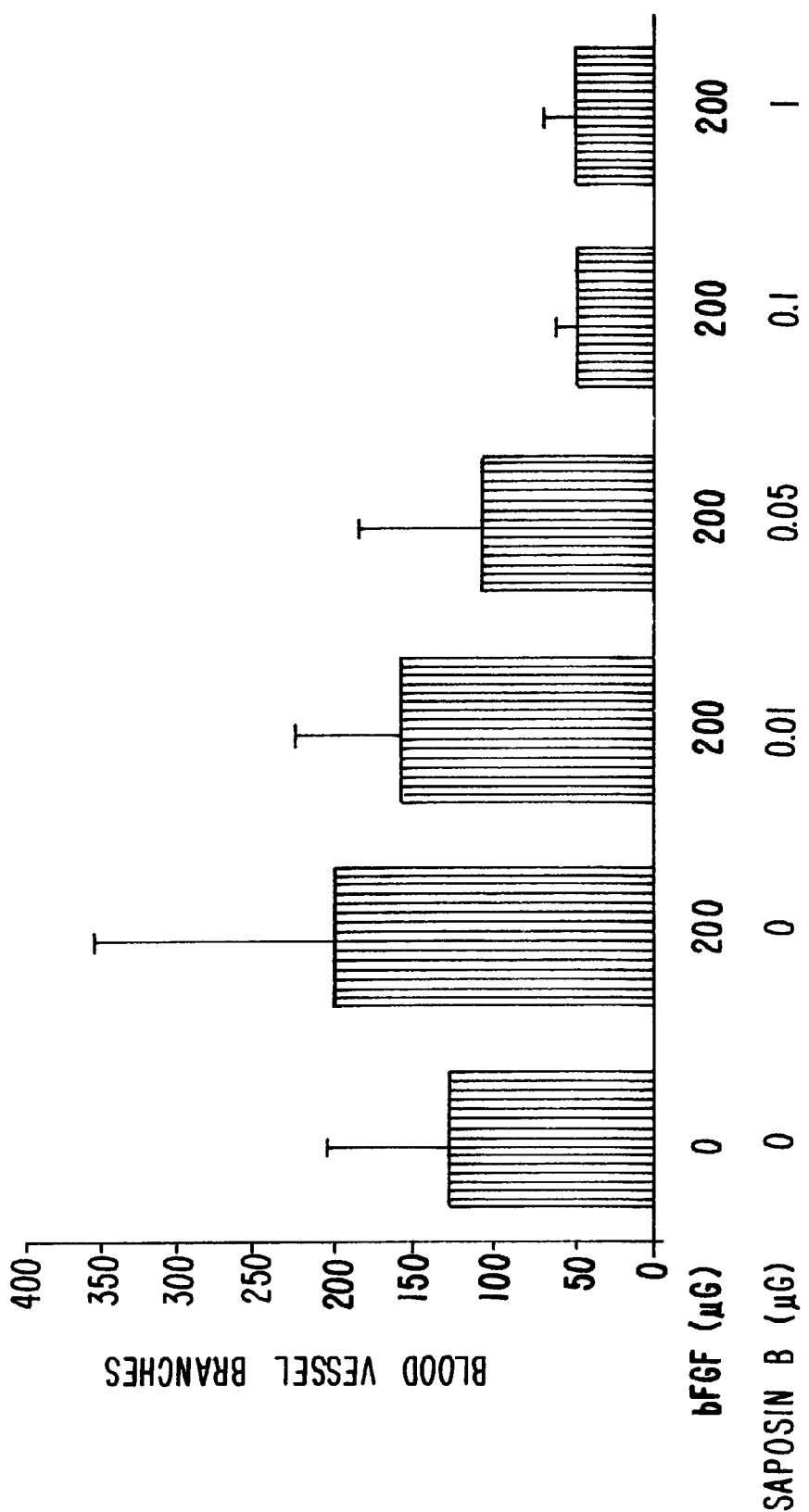
FIG. 3: Effect of recombinant Saposin B angiogenesis. The number of blood vessel branches formed in CAMs in response to angiogenic factor (bFGF) in inhibited by Saposin B in a dose-dependent fashion.

Recombinant Saposin B effectively blocked angiogenesis induced by VEGF or bFGF. See FIG. 3. Moreover, the inhibition of angiogenesis induced by both proteins was blocked by adding anti-Saposin B antibodies to the filter paper. These results demonstrate that Saposin B has anti-angiogenic activity in the CAM assay.

Example 4
Saposin B is Cytotoxic to CD34+/Flk-1+ Cells

A bone marrow derived human CD34+/Flk-1+ progenitor cell can be mobilized into the blood stream in response to tumor induced signals such as VEGF and cytokine production. These cells can target to sites of angiogenesis where they mature into activated endothelial cells and thus contribute to the generation of new blood vessels at the tumor site. By blocking the production of these cells or by targeting these cells (i.e., the CD34+/Flk-1+ progenitors and the activated endothelial cell they can become), the angiogenesis/vasculogenesis required for tumor growth can be reduced or halted. CD34+/Flk-1+ selected subpopulations of bone marrow derived stem cells or peripheral mononuclear blood cells have been shown to differentiate into vascular endothelial cells when plated on fibronectin-coated dishes as described in Asahara, et al. *Science* 1997, 275, 965–967. The adherent cells take on a spindle-shaped morphology characteristic of the activated vascular endothelial cells typical of the angiogenic process. These cells express endothelial-specific markers including factor VIII, ulex europaeus agglutinin-1 (UEA-1), endothelial constitutive nitric oxide synthase (ecNOS), and E selectin. Further, when these cells (peripheral blood Flk+ progenitors) are infused into mice, they incorporate into newly formed blood vessels at site of injury. These observation identify CD34+/Flk-1+ bone marrow derived progenitors as a putative precursor to vascular endothelial cells. Preventing these cells from colonizing at distal sites of angiogenesis in tumors has enormous implication for the treatment of tumors.

To determine whether Saposin B was cytotoxic to $CD34^+/Flk\text{-}1^+$ progenitors, $CD34^+/Flk\text{-}1^+$ cells from cord blood were isolated and plated on fibronectin coated dishes in the presence or absence of 50 ng/mL Saposin B. In the absence of Saposin B, adherent cells were observed to proliferate and mature into spindle shaped endothelial cells. However in the presence of Saposin B, $CD34^+/Flk\text{-}1^+$ progenitor grwptj was inhibited.

Saposin B was found not to be toxic to most $CD34^+$ cord blood derived cells, since the difference in viability of Saposin B treated $CD34^+$ cells was only around 20% when compared to control cells. Thus Saposin B not only targets fully differentiated and activated endothelial cells, but also a circulating progenitor, previously shown to target angiogenic sites.

Example 5
Effect of Saposin B on Bone Marrow Progenitor Cells

Human bone marrow cells and peripheral blood mononuclear cells were harvested from a subject after the administration of high doses of cyclophosphamide and G-CSF. Stem cell clonogenic assays in methylcellulose were performed with IL-3, erythropoietin, and VEGF (10 ng/mL, and 100 ng/mL). VEGF was used to determine if there are progenitor cells with self replication capacity but without adherence to extracellular matrix such as fibronectin. It was also desirable to determine if Saposin B was toxic to endothelial cell specific progenitors for hematopoietic (myeloid or erythroid) lineage cells.

It was found that VEGF treatment resulted in the formation of colonies in methylcellulose, thus proving there are progenitor cells responsive to VEGF. These colonies contained mixture of cells indicating more than one cell lineage generated in response to VEGF. The colonies also contained spindle shaped cells which mark the presence of VEGF receptors.

Saposin B treatment had no cytotoxic effect on the colonies developed with either IL-3 or erythropoietin, suggesting that Saposin B is not toxic to these cell types. However, colonies generated with VEGF had loss of spindle shaped cells, while round compact cells remained. This indicated that Saposin B was toxic to endothelial cells with VEGF receptors; cells likely to engage in the angiogenic and vasculogenic processes.

Example 6
Saposin B Is Active In vivo

In order to determine the anti-angiogenic activity of the recombinant Saposin B, tumor cells were implanted in immuno-deficient mice and treated with either Saposin B or buffer alone.

Nude mice were injected with $2\times10^6$ KS-SLK or KS Y-1 cells subcutaneously in a total volume of 100 μL. After one week of tumor development, the mice were injected subcutaneously daily with either PBS or Saposin B at concentrations of 1, 10 and 20 mg/kg for a total protein concentration of 100 μg/kg body weight. The tumor size was measured three times a week. The results represent the median of 4 mice in each group.

Tumor growth was markedly retarded by Saposin B, and the effect was dose dependent. Saposin B had no effect on the growth of these cells. Thus, Saposin B is a potent anti-tumor protein with activity both in vitro and in vivo.

Figure 4:
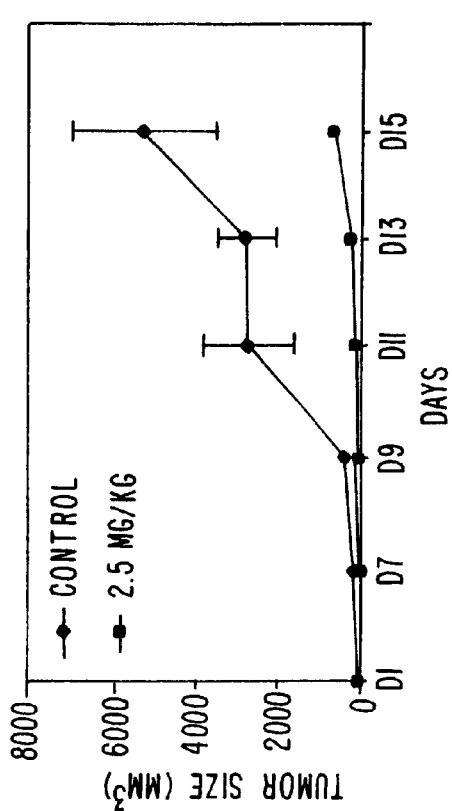
FIG. 4: Inhibition of tumor growth in mice. C57BL/6 mice were implanted with Lewis lung carcinoma, melanoma (B16), and T-cell lymphoma (EL4). KS Y-1 was implanted in nude mice as a positive control. One day after implantation 2.5 mg/kg of Saposin B was injected into the mice subcutaneously.
Figure 4:
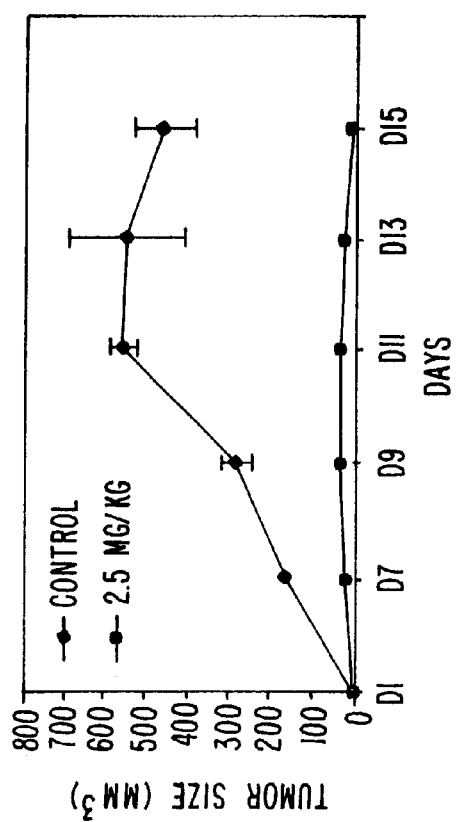
Figure 4:
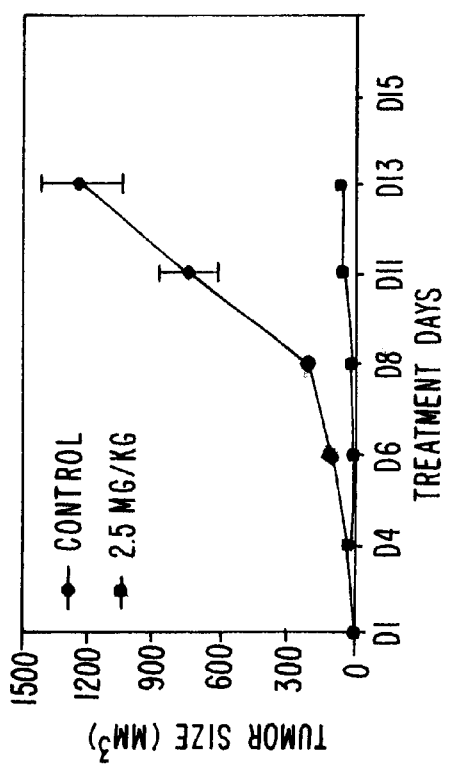
Figure 4:
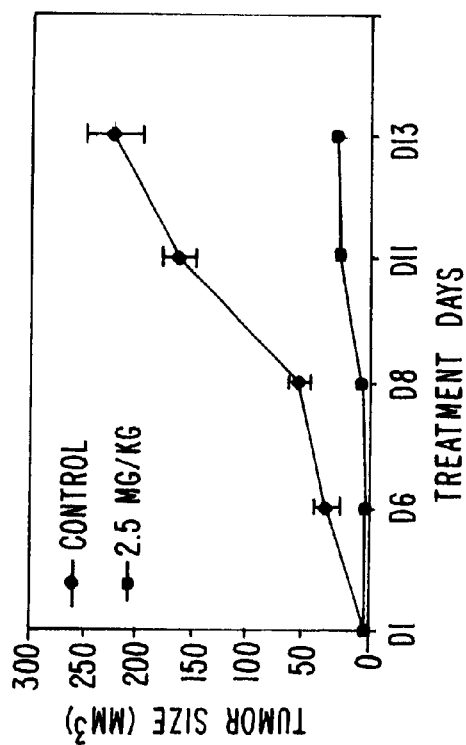

To determine whether this anti-tumor effect was reproducible with different classes of syngeneic tumors, C57BL/6 mice were implanted with Lewis lung carcinoma, melanoma (B16), and T-cell lymphoma (EL-4) cell lines. KS Y-1 was implanted into nude mice for a positive control. The day following tumor implantation, 2.5 mg/kg of Saposin B was administered intraperitoneally. Tumor size was measured three times a week for two weeks at which time the mice were sacrificed for analysis. Saposin B treated mice showed a profound inhibition of tumor growth in all tumor types tested. See, FIG. 4

Figure 5:
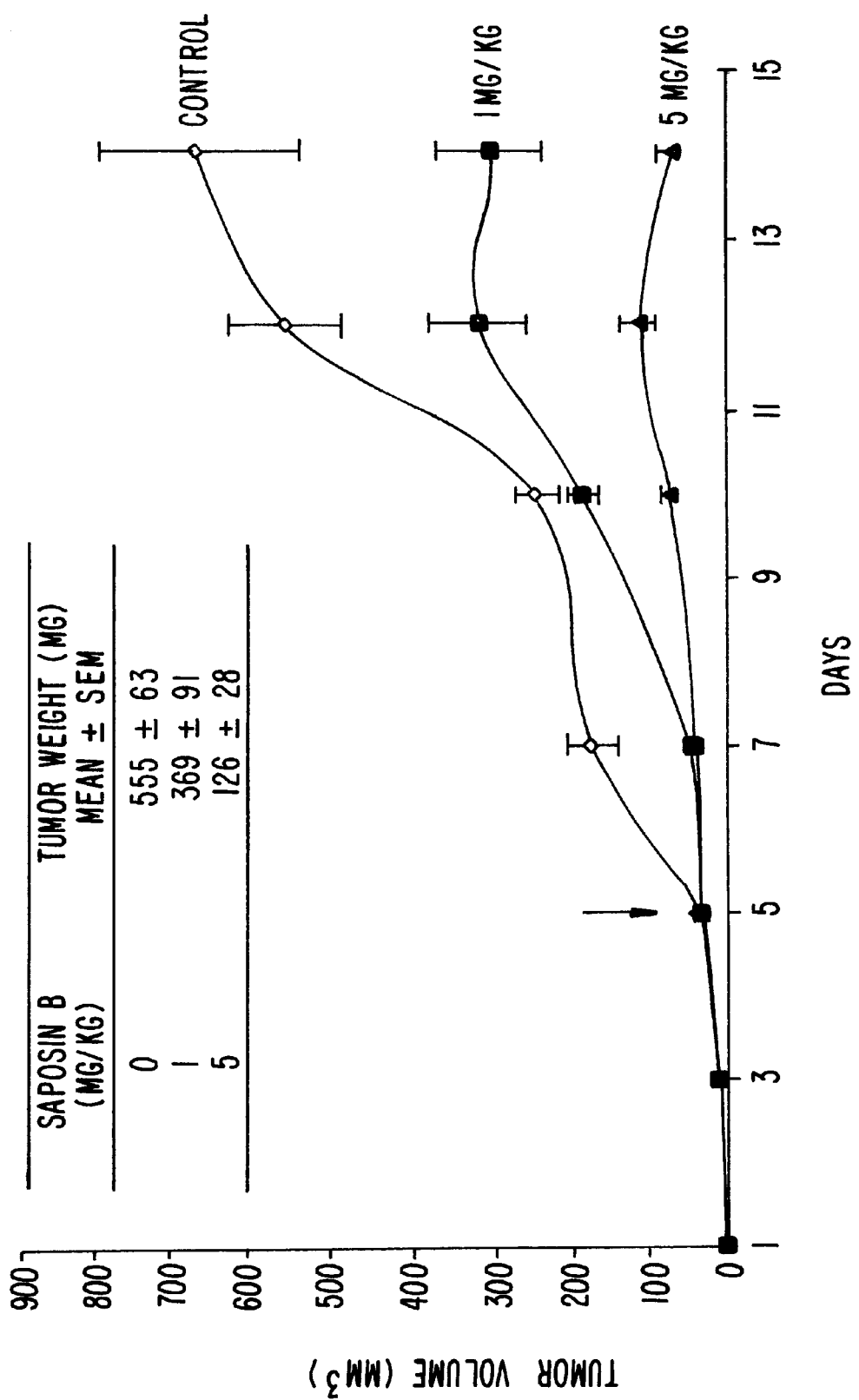
FIG. 5: Effect of two daily doses of Saposin B on growth of an established KS Y-1 tumor. The arrow marks initiation of daily subcutaneous dosing.

In further experiments, KS tumors were allowed to grow for five days before treatment with Saposin B (1 and 5 mg/kg daily at a distal site from the timor). In control mice, tumors grew to a weight of 555±mg. Inhibition of tumor growth was observed in Saposin B treated mice with weights of excised tumors being approximately 23% that of controls. See FIG. 5. Tumors excised at the conclusion of the experiments were also examined for apoptosis, blood vessel density, andmitotic index. Saposin B treated tumors showed an increase in apoptosis and decrease in blood vessel density. Thus, contrary to the results in vitro, Saposin B has an inhibitory effect against non-KS tumors.

Example 7
Anti-Angiogenic Activity of Saposin B Polypeptides

To determine if Saposin B polypeptides had anti-angiogenic activity, a series of overlapping polypeptides were synthesized and tested in the KS Y-1 cell proliferation assay. The overlapping polypeptides are SEQ ID NOS:13 though 42. The results are tabulated in Tables 4 through 8. Cell Proliferation assays in either KS cells or fibroblast. Cells were plated in 48 well plates at equal numbers in appropriate culture medium. Cells were treated with the test compounds at various concentrations on day one, and on day 3. MTT was done on day 5. KS cells were used to represent the activated endothelial cells, while fibroblast cells represent the control cells. The results are remarkable for the lack of toxicity to the fibroblast relative to the activated endothelial cells/KS cells. Similar results were seen in proliferating endothelial cells. These results support the findings of antiangiogenic properties of these test compounds.

TABLE 4

KS Cell Proliferation in the Presence of Saposin B Polypeptides[1]

| | Control | % of Control | | | | | |
|---|---|---|---|---|---|---|---|
| | OD$_{490\,nm}$ | 1 µg/mL | 5 µg/mL | 10 µg/ml | 50 µg/mL | 100 µg/mL | 500 µg/mL |
| SEQ ID NO:13 | 0.56 | 51.8 | | 17.9 | 1.8 | 1.8 | 1.8 |
| SEQ ID NO:14 | 0.56 | | | 89.3 | | 60.7 | 28.6 |
| SEQ ID NO:15 | 0.56 | | | 101.8 | | 60.7 | 28.6 |
| SEQ ID NO:17 | | | | 96.3 | | 86.4 | 46.9 |
| SEQ ID NO:18 | 0.81 | | | 88.9 | | 86.4 | 58.0 |
| SEQ ID NO:20 | 0.56 | 100.0 | 96.4 | 92.9 | 82.1 | | |
| SEQ ID NO:21 | 1.15 | 88.7 | 68.7 | 26.1 | 7.0 | | |
| SEQ ID NO:22 | 1.15 | 158.3 | 77.4 | 59.1 | 37.4 | | |
| SEQ ID NO:23 | 1.15 | 88.7 | 83.5 | 68.7 | 51.3 | | |

[1]Cell proliferation assay performed with 7,500 KS Y-1 cells/well in 48-well plates. Incubation for 5 days at 37° C. MTT added and plates read as described in the text.

TABLE 5

Fibroblast Proliferation in the Presence of Saposin B Polypeptides[2]

| | Control | % of Control | | |
|---|---|---|---|---|
| | OD$_{490-650}$ nm | 1 µg/mL | 10 µg/mL | 50 µg/mL |
| SEQ ID NO: 19 | 0.23 | 91.3 | 91.3 | 82.6 |
| SEQ ID NO: 20 | 0.23 | 91.3 | 95.7 | 95.7 |
| SEQ ID NO: 21 | 0.23 | 100.0 | 91.3 | 87.0 |
| SEQ ID NO: 22 | 0.23 | 95.7 | 95.7 | 87.0 |

[2]Cell proliferation assay performed with 5000 T1 cells/well in 48-well plates. Incubation for 7 days at 37° C. MTT added and plates read as described in the text.

TABLE 6

Effect of SEQ ID NO: 19 Saposin B polypeptide on Migration of KS Cell Lines[3]

| SEQ ID NO: 19 | % Cells Migrating Through Membrane (of Control) |
|---|---|
| 0 µg/mL (control) | 100 |
| 1 µg/mL | 78.23 |
| 10 µg/L | 40.32 |
| 50 µg/mL | 20.98 |

[3]Cell migration assay was performed with 50,000 KS Y-1 cells/well. Wells were coated with fibronectin prior to use. 25 ng/mL bFGF was added to the lower chamber to act as a chemotactic agent. cells counted after overnight incubation with polypeptide.

Positive results from the polypeptide represented as SEQ ID NO:19 suggested that other, smaller polypeptides within that region would also have activity. The results of cell proliferation assays using smaller polypeptides of SEQ ID NOS:19–31 are tabulated in Table 7.

TABLE 7

Cell Proliferation in the Presence of Saposin B Polypeptides[4]

| | Cell Proliferation Activity (% of control) | | | |
|---|---|---|---|---|
| SEQ ID NO: | KSY-1 | | T1 | |
| SEQ ID NO: 19 | 28 | | 8 | |
| SEQ ID NO: 20 | 93 | | 84 | |
| SEQ ID NO: 21 | 29 | | 67 | |
| SEQ ID NO: 22 | 59 | | 28 | |
| SEQ ID NO: 23 | 68 | | 51 | |
| SEQ ID NO: 24 | 68 | 46 | 96 | 84 |
| SEQ ID NO: 25 | 72 | 39 | 98 | 89 |
| SEQ ID NO: 26 | 72 | 40 | 96 | 81 |
| SEQ ID NO: 27 | 60 | 22 | 88 | 75 |
| SEQ ID NO: 28 | 30 | 10 | 91 | 87 |
| SEQ ID NO: 29 | 65 | 33 | 95 | 86 |
| SEQ ID NO: 30 | 77 | 35 | 92 | 84 |
| SEQ ID NO: 31 | 74 | | 87 | 80 |

[4]Cell proliferation performed with fibroblast T1 cells/well in 48-well plates. Incubation for 5 days at 37° C. MTT added and plates read as described in the text.

TABLE 8

Saposin B Peptides Activity Summary

| Name | Core Lab code/group | Seq ID NO: | Sequence | IC$_{50}$ (mM) Activity in KS Y-1 |
|---|---|---|---|---|
| | internal peptide scan | | | |
| G1-V11 | 20PG | 19 | GDVCQDCIQMV | 4.9 |
| Q9-F15 | 2PG | 43 | QMVTDIQTQVRTNSTF | 14 |
| S23-R39 | 3PG | 15 | STFVQALVEHVKEECDR | 22 |
| C37-S53 | 4PG | 42 | CDRLGPGMAKICKNYIS | 9.7 |
| Y51-P68 | 5PG | 17 | YISQYSEIAIQMMMHMQP | 20 |

TABLE 8-continued

Saposin B Peptides Activity Summary

| Name | Core Lab code/group | Seq ID NO: | Sequence | IC$_{50}$ (mM) Activity in KS Y-1 |
|---|---|---|---|---|
| Q67-E80 | 36PG | 41 | QPKEICALVGFCDEVK | 14 |
| | Bisection of 20PG | | | |
| G1-Q5 | 23PG | 22 | GDVCQ | 49.4 |
| D6-V12 | 24PG | 23 | DCIQMV | 57.3 |
| | C-terminal deletions | | | |
| D2-M10 | 25PG | 24 | DVCQDCIQM | 16.2 |
| D2-Q9 | 26PG | 25 | DVCQDCIQ | 16.6 |
| D2-I8 | 27PG | 26 | DVCQDCI | 20 |
| D2-C7 | 28PG | 27 | DVCQDC | 19 |
| D2-D6 | 29PG | 28 | DVCQD | 11.8 |
| | N-terminal deletions | | | |
| D2-V11 | 22PG | 21 | DVCQDCIQMV | 4.4 |
| V3-V11 | 30PG | 29 | VCQDCIQMV | 11.9 |
| C4-V11 | 31PG | 30 | CQDCIQMV | 13.2 |
| Q5-V11 | 32PG | 31 | QDCIQMV | 16.6 |
| | C-S mutations | | | |
| G1-(S4,S7)-V11 | 21PG | 20 | GDVSQDSIQMV | >400 |
| G1-(S4)-VI1 | 33PG | 32 | GDVSQDCIQMV | 18 |
| G1-(S7)-V11 | 34PG | 33 | GDVCQDSIQMV | 7.8 |
| G1-(S4)-D6 | 35PG | 34 | GDVSQD | 40 |
| | V3 and Q5 mutations | | | |
| D2-(A3)-D6 | 37PG | 35 | DACQD | 42.9 |
| D2-(I3)-D6 | 38PG | 36 | DICQD | 34.6 |
| D2-(L3)-D6 | 39PG | 37 | DLCQD | 39.8 |
| D2-(S5)-D6 | 40PG | 38 | DVCSD | 25.5 |
| D2-(E5)-D6 | 41PG | 39 | DVCEb | 26.3 |
| D2-(D5)-D6 | 42PG | 40 | DVCDD | 12.2 |

Figure 6:
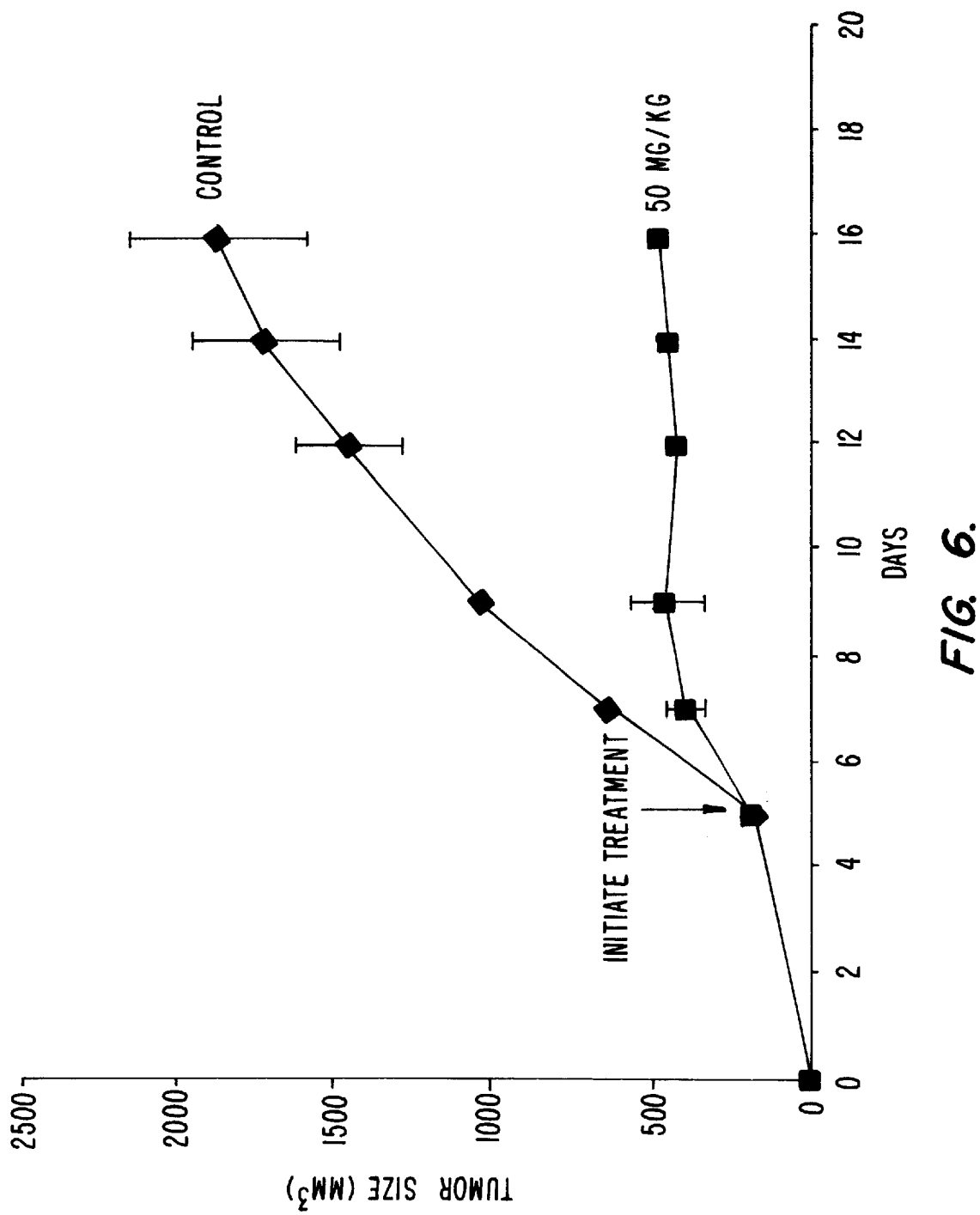
FIG. 6: Effect of pentapeptide DVCQD (SEQ ID NO:28) on the growth of estiblished KS Y-1 tumors in mice. Mice were implanted with the tumor on day one. Treatment with the peptide was started on the following day at a dose of 50 mg/kg subcutaneously daily. When compared to the control, the tumor volumes were significantly smaller.Ther arrow marks initiation of daily subcutaneous dosing.

In vivo results for experiments similar to those described in Example 6 demonstrate that the pentapeptide DVCQD (SEQ ID NO:28) was active in vivo (see FIG. 6).

What is claimed is:

1. A method of treating a mammal, wherein said mammal has a disease or pathological condition caused or worsened by blood vessel growth or formation, by administering an amount of an isolated polypeptide, said polypeptide being from about 5 to about 80 amino acids in length and comprising an N-terminal contiguous amino acid sequence DVCQD (SEQ ID NO: 28), and wherein said polypeptide has antiangiogenic activity and said amount of polypeptide is effective to reduce angiogenesis.

2. The method of claim 1, wherein said mammal is human.

3. The method of claim 1, wherein said disease or pathological condition is cancer.

4. The method of claim 3, wherein said cancer is Kaposi's Sarcoma.

5. The method of claim 1, wherein said blood vessel growth or formation is in eye tissue.

6. The method of claim 1, wherein said disease or pathological condition is retrolental fibroplasia.

7. The method of claim 1, wherein administration is selected from the group consisting of subcutaneous, intramuscular, intravenous, intra-arterial, intrabronchial, intraocular, rectal, vaginal, intranasal and sublingual.

8. The method of claim 1, wherein said administration is selected from the group consisting of intralesional and transdermal.

9. The method of claim 1, wherein said isolated polypeptide is Saposin B.

10. The method of claim 1, wherein said isolated polypeptide is DVCQD (SEQ ID NO: 28).

11. The method of claim 1, wherein said effective amount is from about 0.1 mg/kg to about 20 mg/kg.

12. A method of treating a mammal, wherein said mammal has a disease or pathological condition caused or worsened by blood vessel growth or formation, by administering an amount of an isolated polypeptide, wherein said polypeptide is DVCQD (SEQ ID NO: 28), and wherein said polypeptide has antiangiogenic activity and said amount of polypeptide is effective to reduce angiogenesis.

13. The method of claim 12, wherein said mammal is human.

14. The method of claim 12, wherein said disease or pathological condition is cancer.

15. The method of claim 14, wherein said cancer is Kaposi's Sarcoma.

16. The method of claim 12, wherein said blood vessel growth or formation is in eye tissue.

17. The method of claim 12, wherein said disease or other pathological condition is retrolental fibroplasia.

18. The method of claim 12, wherein administration is selected from the group consisting of subcutaneous, intramuscular, intravenous, intra-arterial, intrabronchial, intraocular, rectal, vaginal, intranasal and sublingual.

19. The method of claim 12, wherein said administration is selected from the group consisting of intralesional and transdermal.

20. The method of claim 12, wherein said effective amount is from about 0.1 mg/kg to about 20 mg/kg.

21. A method of treating a mammal, wherein said mammal has a disease or pathological condition caused or worsened by blood vessel growth or formation, by administering an amount of an isolated polypeptide, wherein said polypeptide is Saposin B, and wherein said polypeptide has antiangiogenic activity and said amount of polypeptide is effective to reduce angiogenesis.

22. The method of claim 21, wherein said mammal is human.

23. The method of claim 21, wherein said disease or pathological condition is cancer.

24. The method of claim 23, wherein said cancer is Kaposi's Sarcoma.

25. The method of claim 21, wherein said blood vessel growth or formation is in eye tissue.

26. The method of claim 21, wherein said disease or pathological condition is retrolental fibroplasia.

27. The method of claim 21, wherein administration is selected from the group consisting of subcutaneous, intramuscular, intravenous, intra-arterial, intrabronchial, intraocular, rectal, vaginal, intranasal and sublingual.

28. The method of claim 21, wherein the administration is selected from the group consisting of intralesional and transdermal.

29. The method of claim 21, wherein said effective amount is from about 0.1 mg/kg to about 20 mg/kg.

30. An isolated polypeptide consisting of DVCQD (SEQ ID NO: 28) and wherein said polypeptide has antiangiogenic activity.

31. An isolated glycosylated polypetide consisting of DVCQD (SEQ ID NO: 28) and wherein said polypeptide has antiangiogenic activity.

32. A composition comprising said isolated polypetide of claim 30 and one or more pharmaceutically acceptable excipients.

33. A composition comprising an amount of said isolated polypeptide of claim 31 and one or more pharmaceutically acceptable excipients.

34. The composition of claim 32, wherein said composition is in unit dosage form.

35. The composition of claim 34, wherein said unit dosage form is an aseptic solution comprising said polypeptide.

36. The composition of claim 34, wherein said unit dosage form is a topical ointment.

37. The composition of claim 33, wherein said composition is in unit dosage form.

38. The composition of claim 37, wherein said unit dosage form is an aseptic solution comprising said polypeptide.

39. The composition of claim 37, wherein said unit dosage form is a topical ointment.

* * * * *

```
                        SEQUENCE LISTING

<160> NUMBER OF SEQ ID NOS: 59

<210> SEQ ID NO 1
<211> LENGTH: 524
<212> TYPE: PRT
<213> ORGANISM: Homo sapiens
<220> FEATURE:
<223> OTHER INFORMATION: prosaposin
<220> FEATURE:
<221> NAME/KEY: PEPTIDE
<222> LOCATION: (195)..(275)
<223> OTHER INFORMATION: Saposin B

<400> SEQUENCE: 1

Met Tyr Ala Leu Phe Leu Leu Ala Ser Leu Leu Gly Ala Ala Leu Ala
 1               5                  10                  15

Gly Pro Val Leu Gly Leu Lys Glu Cys Thr Arg Gly Ser Ala Val Trp
             20                  25                  30

Cys Gln Asn Val Lys Thr Ala Ser Asp Cys Gly Ala Val Lys His Cys
         35                  40                  45

Leu Gln Thr Val Trp Asn Lys Pro Thr Val Lys Ser Leu Pro Cys Asp
     50                  55                  60
```

```
Ile Cys Lys Asp Val Val Thr Ala Ala Gly Asp Met Leu Lys Asp Asn
 65                  70                  75                  80

Ala Thr Glu Glu Glu Ile Leu Val Tyr Leu Glu Lys Thr Cys Asp Trp
                 85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
        435                 440                 445

Lys Gln Cys Asp Gln Phe Val Ala Glu Tyr Glu Pro Val Leu Ile Glu
    450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
```

```
                    485                 490                 495
Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
        515                 520

<210> SEQ ID NO 2
<211> LENGTH: 81
<212> TYPE: PRT
<213> ORGANISM: Homo sapiens
<220> FEATURE:
<223> OTHER INFORMATION: Saposin B

<400> SEQUENCE: 2

Gly Asp Val Cys Gln Asp Cys Ile Gln Met Val Thr Asp Ile Gln Thr
 1               5                  10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu Val
65                  70                  75                  80

Lys

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:5' primer
      for amplifying Saposin B cDNA

<400> SEQUENCE: 3
attcgaattc aaggggacgt ttgccaggac tgc                               33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:3' primer
      for amplifying Saposin B cDNA

<400> SEQUENCE: 4
ttctgtgatg aggtgaaata gctcgagctc gag                               33

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:5' primer
      for PCR amplification of Prosaposin

<400> SEQUENCE: 5
ctagatctag aaatgtacgc cctcttcctc ctggcc                            36

<210> SEQ ID NO 6
<211> LENGTH: 36
<212> TYPE: DNA
<213> ORGANISM: Artificial Sequence
```

<220> FEATURE:
<223> OTHER INFORMATION: Description of Artificial Sequence:3' primer
      for PCR amplification of Prosaposin

<400> SEQUENCE: 6
ctcgagctcg agctagttcc acacatggcg tttgca                    36

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:5' primer
      for PCR amplification of Saposin A

<400> SEQUENCE: 7
ctagatctag aatcccttcc ctgcgacata tcc                       33

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:3' primer
      for PCR amplification of Saposin A

<400> SEQUENCE: 8
ctcgagctcg agtcacttct ggagagactc gcagag                    36

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:5' primer
      for PCR amplification of Saposin C

<400> SEQUENCE: 9
ctagatctag aatctgatgt ttactgtgag gtg                       33

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:3' primer
      for PCR amplification of Saposin C

<400> SEQUENCE: 10
ctcgagctcg agtcatgcca gagcagaggt gcagca                    36

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:5' primer
      for PCR amplification of Saposin D

<400> SEQUENCE: 11
ctagatctag aagacggtgg cttctgcgaa gtg                       33

<210> SEQ ID NO 12
<211> LENGTH: 36
<212> TYPE: DNA
<213> ORGANISM: Artificial Sequence
<220> FEATURE:

```
<223> OTHER INFORMATION: Description of Artificial Sequence:3' primer
      for PCR amplification of Saposin D

<400> SEQUENCE: 12
ctcgagctcg agtcacttat gggccgaggg gcaggc                                    36

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:
      anti-angiogenic polypeptide

<400> SEQUENCE: 13

Gln Pro Lys Asp Asn Gly Asp Val Cys Gln Asp Cys Ile Gln Val
 1               5                  10                  15

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence:
      anti-angiogenic polypeptide

<400> SEQUENCE: 14

Ile Gln Met Val Thr Asp Ile Gln Thr Ala Val Arg Thr Asn Ser Thr
 1               5                  10                  15
Phe

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence:S23-R39
      anti-angiogenic polypeptide

<400> SEQUENCE: 15

Ser Thr Phe Val Gln Ala Leu Val Glu His Val Lys Glu Glu Cys Asp
 1               5                  10                  15
Arg

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence:
      anti-angiogenic polypeptide

<400> SEQUENCE: 16

Cys Asp Arg Leu Gly Pro Gly Met Ala Asp Lys Asn Tyr Ser
 1               5                  10

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence:Y51-P68
      anti-angiogenic polypeptide

<400> SEQUENCE: 17

Tyr Ile Ser Gln Tyr Ser Glu Ile Ala Ile Gln Met Met Met His Met
```

-continued

```
                1               5                  10                 15
Gln Pro

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide

<400> SEQUENCE: 18

Gln Met Met Met His Met Gln Pro Lys Glu Ile Cys Ala Leu Val Gly
  1               5                  10                 15

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence:G1-V11
      anti-angiogenic polypeptide

<400> SEQUENCE: 19

Gly Asp Val Cys Gln Asp Cys Ile Gln Met Val
  1               5                  10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence:
      G1-(S4, S7)-V11 anti-angiogenic polypeptide

<400> SEQUENCE: 20

Gly Asp Val Ser Gln Asp Ser Ile Gln Met Val
  1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:D2-V11
      anti-angiogenic polypeptide

<400> SEQUENCE: 21

Asp Val Cys Gln Asp Cys Ile Gln Met Val
  1               5                  10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:G1-Q5
      anti-angiogenic polypeptide

<400> SEQUENCE: 22

Gly Asp Val Cys Gln
  1               5

<210> SEQ ID NO 23
<211> LENGTH: 6
<212> TYPE: PRT
<213> ORGANISM: Artificial Sequence
```

```
<220> FEATURE:
<223> OTHER INFORMATION: Description of Artificial Sequence:D6-V12
      anti-angiogenic polypeptide

<400> SEQUENCE: 23

Asp Cys Ile Gln Met Val
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:D2-M10
      anti-angiogenic polypeptide

<400> SEQUENCE: 24

Asp Val Cys Gln Asp Cys Ile Gln Met
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:D2-Q9
      anti-angiogenic polypeptide

<400> SEQUENCE: 25

Asp Val Cys Gln Asp Cys Ile Gln
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:D2-I8
      anti-angiogenic polypeptide

<400> SEQUENCE: 26

Asp Val Cys Gln Asp Cys Ile
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:D2-C7
      anti-angiogenic polypeptide

<400> SEQUENCE: 27

Asp Val Cys Gln Asp Cys
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:D2-D6
      anti-angiogenic polypeptide

<400> SEQUENCE: 28

Asp Val Cys Gln Asp
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:V3-V11
      anti-angiogenic polypeptide

<400> SEQUENCE: 29

Val Cys Gln Asp Cys Ile Gln Met Val
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:C4-V11
      anti-angiogenic polypeptide

<400> SEQUENCE: 30

Cys Gln Asp Cys Ile Gln Met Val
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:Q5-V11
      anti-angiogenic polypeptide

<400> SEQUENCE: 31

Gln Asp Cys Ile Gln Met Val
 1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence:G1-(S4)-V11
      anti-angiogenic polypeptide

<400> SEQUENCE: 32

Gly Asp Val Ser Gln Asp Cys Ile Gln Met Val
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence:G1-(S7)-V11
      anti-angiogenic polypeptide

<400> SEQUENCE: 33

Gly Asp Val Cys Gln Asp Ser Ile Gln Met Val
 1               5                  10

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:G1-(S4)-D6
      anti-angiogenic polypeptide
```

-continued

```
<400> SEQUENCE: 34

Gly Asp Val Ser Gln Asp
  1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:D2-(A3)-D6
      anti-angiogenic polypeptide

<400> SEQUENCE: 35

Asp Ala Cys Gln Asp
  1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:D2-(I3)-D6
      anti-angiogenic polypeptide

<400> SEQUENCE: 36

Asp Ile Cys Gln Asp
  1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence:D2-(L3)-D6
      anti-angiogenic polypeptide

<400> SEQUENCE: 37

Asp Leu Cys Gln Asp
  1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence:D2-(S5)-D6
      anti-angiogenic polypeptide

<400> SEQUENCE: 38

Asp Val Cys Ser Asp
  1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence:D2-(E5)-D6
      anti-angiogenic polypeptide

<400> SEQUENCE: 39

Asp Val Cys Glu Asp
  1               5

<210> SEQ ID NO 40
<211> LENGTH: 5
<212> TYPE: PRT
```

```
<213> ORGANISM: Artificial Sequence
<220> FEATURE:
<223> OTHER INFORMATION: Description of Artificial Sequence:D2-(D5)-D6
      anti-angiogenic polypeptide

<400> SEQUENCE: 40

Asp Val Cys Asp Asp
 1               5

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence:Q67-E80
      anti-angiogenic polypeptide

<400> SEQUENCE: 41

Gln Pro Lys Glu Ile Cys Ala Leu Val Gly Phe Cys Asp Glu Val Lys
 1               5                  10                  15

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence:C37-S53
      anti-angiogenic polypeptide

<400> SEQUENCE: 42

Cys Asp Arg Leu Gly Pro Gly Met Ala Lys Ile Cys Lys Asn Tyr Ile
 1               5                  10                  15

Ser

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence:Q9-F15
      anti-angiogenic polypeptide

<400> SEQUENCE: 43

Gln Met Val Thr Asp Ile Gln Thr Gln Val Arg Thr Asn Ser Thr Phe
 1               5                  10                  15

<210> SEQ ID NO 44
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(6)
<223> OTHER INFORMATION: Xaa = any amino acid, Xaa at positions 1-6 may
      be present or absent
<220> FEATURE:
<221> NAME/KEY: MOD_RES
<222> LOCATION: (12)..(70)
<223> OTHER INFORMATION: Xaa = any amino acid, Xaa at positions 12-70
      may be present or absent

<400> SEQUENCE: 44

Xaa Xaa Xaa Xaa Xaa Xaa Asp Val Cys Gln Asp Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
```

```
                    20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa
 65                  70

<210> SEQ ID NO 45
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(5)
<223> OTHER INFORMATION: Xaa = any amino acid
<220> FEATURE:
<221> NAME/KEY: MOD_RES
<222> LOCATION: (1)..(4)
<223> OTHER INFORMATION: Xaa at positions 1-4 may be present or absent
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(70)
<223> OTHER INFORMATION: Xaa = any amino acid, Xaa at positions 12-70
      may be present or absent

<400> SEQUENCE: 45

Xaa Xaa Xaa Xaa Xaa Xaa Asp Val Cys Gln Asp Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
 65                  70

<210> SEQ ID NO 46
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (12)..(70)
<223> OTHER INFORMATION: Xaa = any amino acid, Xaa at positions 12-70
      may be present or absent

<400> SEQUENCE: 46

Gln Pro Lys Asp Asn Xaa Asp Val Cys Gln Asp Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45
```

```
Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
    65                  70

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(6)
<223> OTHER INFORMATION: Xaa = any amino acid, Xaa at positions 1-6 may
      be present or absent
<220> FEATURE:
<221> NAME/KEY: MOD_RES
<222> LOCATION: (12)..(16)
<223> OTHER INFORMATION: Xaa = any amino acid
<220> FEATURE:
<221> NAME/KEY: MOD_RES
<222> LOCATION: (13)..(16)
<223> OTHER INFORMATION: Xaa at positions 13-16 may be present or absent

<400> SEQUENCE: 47

Xaa Xaa Xaa Xaa Xaa Xaa Asp Val Cys Gln Asp Xaa Xaa Xaa Xaa Xaa
  1               5                  10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(6)
<223> OTHER INFORMATION: Xaa = any amino acid, Xaa at positions 1-6 may
      be present or absent

<400> SEQUENCE: 48

Xaa Xaa Xaa Xaa Xaa Xaa Asp Val Cys Gln Asp Cys Ile Gln Met Val
  1               5                  10                  15

<210> SEQ ID NO 49
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (2)..(5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(70)
<223> OTHER INFORMATION: Xaa = any amino acid, Xaa at positions 12-70
      may be present or absent

<400> SEQUENCE: 49

Gln Xaa Xaa Xaa Xaa Xaa Asp Val Cys Gln Asp Xaa Xaa Xaa Xaa Xaa
  1               5                  10                  15
```

```
Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa
 65                 70

<210> SEQ ID NO 50
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)
<223> OTHER INFORMATION: Xaa = any amino acid, Xaa at position 1 may be
      present or absent
<220> FEATURE:
<221> NAME/KEY: MOD_RES
<222> LOCATION: (3)..(5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(70)
<223> OTHER INFORMATION: Xaa = any amino acid, Xaa at positions 12-70
      may be present or absent

<400> SEQUENCE: 50

Xaa Pro Xaa Xaa Xaa Xaa Asp Val Cys Gln Asp Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa
 65                 70

<210> SEQ ID NO 51
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(2)
<223> OTHER INFORMATION: Xaa = any amino acid, Xaa at positions 1 and 2
      may be present or absent
<220> FEATURE:
<221> NAME/KEY: MOD_RES
<222> LOCATION: (4)..(5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
```

```
<222> LOCATION: (12)..(70)
<223> OTHER INFORMATION: Xaa = any amino acid, Xaa at positions 12-70
      may be present or absent

<400> SEQUENCE: 51

Xaa Xaa Lys Xaa Xaa Xaa Asp Val Cys Gln Asp Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
      50                  55                  60

Xaa Xaa Xaa Xaa Xaa Xaa
 65                  70

<210> SEQ ID NO 52
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(3)
<223> OTHER INFORMATION: Xaa = any amino acid, Xaa at positions 1-3 may
      be present or absent
<220> FEATURE:
<221> NAME/KEY: MOD_RES
<222> LOCATION: (5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(70)
<223> OTHER INFORMATION: Xaa = any amino acid, Xaa at positions 12-70
      may be present or absent

<400> SEQUENCE: 52

Xaa Xaa Xaa Asp Xaa Xaa Asp Val Cys Gln Asp Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
      50                  55                  60

Xaa Xaa Xaa Xaa Xaa Xaa
 65                  70

<210> SEQ ID NO 53
<211> LENGTH: 70
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(4)
<223> OTHER INFORMATION: Xaa = any amino acid, Xaa at positions 1-4 may
      be present or absent
<220> FEATURE:
```

```
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(70)
<223> OTHER INFORMATION: Xaa = any amino acid, Xaa at positions 12-70
      may be present or absent

<400> SEQUENCE: 53

Xaa Xaa Xaa Xaa Asn Xaa Asp Val Cys Gln Asp Xaa Xaa Xaa Xaa Xaa
 1               5                  10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa
 65                  70

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(4)
<223> OTHER INFORMATION: Xaa = any amino acid, Xaa at positions 1-4 may
      be present or absent
<220> FEATURE:
<221> NAME/KEY: MOD_RES
<222> LOCATION: (5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)
<223> OTHER INFORMATION: Xaa = any amino acid
<220> FEATURE:
<221> NAME/KEY: MOD_RES
<222> LOCATION: (13)..(16)
<223> OTHER INFORMATION: Xaa = any amino acid, Xaa at positions 13-16
      may be present or absent

<400> SEQUENCE: 54

Xaa Xaa Xaa Xaa Xaa Xaa Asp Val Cys Gln Asp Xaa Xaa Xaa Xaa Xaa
 1               5                  10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(4)
<223> OTHER INFORMATION: Xaa = any amino acid, Xaa at positions 1-4 may
      be present or absent
<220> FEATURE:
<221> NAME/KEY: MOD_RES
<222> LOCATION: (5)
<223> OTHER INFORMATION: Xaa = any amino acid
```

```
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (13)..(16)
<223> OTHER INFORMATION: Xaa = any amino acid, Xaa at positions 13-16
      may be present or absent

<400> SEQUENCE: 55

Xaa Xaa Xaa Xaa Xaa Xaa Asp Val Cys Gln Asp Cys Xaa Xaa Xaa Xaa
 1               5                  10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(4)
<223> OTHER INFORMATION: Xaa = any amino acid, Xaa at positions 1-4 may
      be present or absent
<220> FEATURE:
<221> NAME/KEY: MOD_RES
<222> LOCATION: (5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)
<223> OTHER INFORMATION: Xaa = any amino acid
<220> FEATURE:
<221> NAME/KEY: MOD_RES
<222> LOCATION: (14)..(16)
<223> OTHER INFORMATION: Xaa = any amino acid, Xaa at positions 14-16
      may be present or absent

<400> SEQUENCE: 56

Xaa Xaa Xaa Xaa Xaa Xaa Asp Val Cys Gln Asp Xaa Ile Xaa Xaa Xaa
 1               5                  10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(4)
<223> OTHER INFORMATION: Xaa = any amino acid, Xaa at positions 1-4 may
      be present or absent
<220> FEATURE:
<221> NAME/KEY: MOD_RES
<222> LOCATION: (5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(13)
<223> OTHER INFORMATION: Xaa = any amino acid
<220> FEATURE:
<221> NAME/KEY: MOD_RES
<222> LOCATION: (15)..(16)
```

```
<223> OTHER INFORMATION: Xaa = any amino acid, Xaa at positions 15 and
      16 may be present or absent

<400> SEQUENCE: 57

Xaa Xaa Xaa Xaa Xaa Xaa Asp Val Cys Gln Asp Xaa Xaa Gln Xaa Xaa
 1               5                  10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(4)
<223> OTHER INFORMATION: Xaa = any amino acid, Xaa at positions 1-4 may
      be present or absent
<220> FEATURE:
<221> NAME/KEY: MOD_RES
<222> LOCATION: (5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(14)
<223> OTHER INFORMATION: Xaa = any amino acid
<220> FEATURE:
<221> NAME/KEY: MOD_RES
<222> LOCATION: (16)
<223> OTHER INFORMATION: Xaa = any amino acid, Xaa at position 16 may
      be present or absent

<400> SEQUENCE: 58

Xaa Xaa Xaa Xaa Xaa Xaa Asp Val Cys Gln Asp Xaa Xaa Xaa Met Xaa
 1               5                  10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence:
      anti-angiogenic polypeptide
<220> FEATURE:
<221> NAME/KEY: MOD_RES
<222> LOCATION: (1)..(4)
<223> OTHER INFORMATION: Xaa = any amino acid, Xaa at positions 1-4 may
      be present or absent
<220> FEATURE:
<221> NAME/KEY: MOD_RES
<222> LOCATION: (5)
<223> OTHER INFORMATION: Xaa = any amino acid
<220> FEATURE:
<221> NAME/KEY: MOD_RES
<222> LOCATION: (6)
<223> OTHER INFORMATION: Xaa = Gly, Ala, Ser or Thr
<220> FEATURE:
<221> NAME/KEY: MOD_RES
<222> LOCATION: (12)..(15)
<223> OTHER INFORMATION: Xaa = any amino acid

<400> SEQUENCE: 59

Xaa Xaa Xaa Xaa Xaa Xaa Asp Val Cys Gln Asp Xaa Xaa Xaa Xaa Val
 1               5                  10                  15
```